(12) United States Patent
Alam et al.

(10) Patent No.: US 9,435,813 B2
(45) Date of Patent: Sep. 6, 2016

(54) BIOMARKERS OF HEMORRHAGIC SHOCK

(75) Inventors: Hasan B. Alam, Natick, MA (US); Yongqing Li, West Roxbury, MA (US)

(73) Assignee: The General Hospital Corporation, Boston, MA (US)

( * ) Notice: Subject to any disclaimer, the term of this patent is extended or adjusted under 35 U.S.C. 154(b) by 34 days.

(21) Appl. No.: 13/696,530

(22) PCT Filed: May 11, 2011

(86) PCT No.: PCT/US2011/036067
§ 371 (c)(1),
(2), (4) Date: Feb. 20, 2013

(87) PCT Pub. No.: WO2011/143308
PCT Pub. Date: Nov. 17, 2011

(65) Prior Publication Data
US 2013/0149713 A1    Jun. 13, 2013

Related U.S. Application Data

(60) Provisional application No. 61/333,475, filed on May 11, 2010.

(51) Int. Cl.
*G01N 33/68* (2006.01)
*G01N 33/15* (2006.01)
*C40B 40/10* (2006.01)
*G01N 33/92* (2006.01)

(52) U.S. Cl.
CPC .......... *G01N 33/6893* (2013.01); *G01N 33/92* (2013.01); *G01N 2800/32* (2013.01)

(58) Field of Classification Search
CPC .......................... G01N 33/6893; G01N 33/92
See application file for complete search history.

(56) References Cited

U.S. PATENT DOCUMENTS

| 2004/0018513 | A1* | 1/2004 | Downing et al. | 435/6 |
| 2005/0074798 | A1* | 4/2005 | Sukumar et al. | 435/6 |
| 2010/0317047 | A1* | 12/2010 | Alam et al. | 435/29 |

FOREIGN PATENT DOCUMENTS

| WO | 2004/063169 | 7/2004 |
| WO | 2004/071401 | 8/2004 |
| WO | 2006/060382 | 6/2006 |
| WO | 2006/117165 | 11/2006 |
| WO | 2007/117272 | 10/2007 |

(Continued)

OTHER PUBLICATIONS

Adams et al., (Shock. Dec. 2002;18(6):513-7).*

(Continued)

*Primary Examiner* — Cherie M Stanfield
(74) *Attorney, Agent, or Firm* — Fish & Richardson P.C.

(57) ABSTRACT

Methods for the use of keratinocyte chemoattractant (KC)/human growth-regulated oncogene (GRO) (KC/GRO), apolipoprotein A2 (APOA2), angiotensinogen r (AGT), thyroglobulin (TG), disintegrin and metalloproteinase domain-containing protein 17 (ADAM17), anionic trypsin-1 (PRSS1), complement C4 (C4A), zona pellucida sperm-binding protein 1 (ZP1), neuropilin-2 (NRP2), solute carrier family 13 member 2 (SLC13A2), glucagon-like peptide 2 receptor (GLP2R), lipoma high mobility group protein isoform I-C (HMGIC) fusion partner-like protein 4 (LHFPL4), and claudin-3 (CLDN3) as biomarkers for diagnosis and prognosis, and for monitoring the efficacy of treatment, in hemorrhagic shock (HS).

25 Claims, 11 Drawing Sheets

(56) References Cited

FOREIGN PATENT DOCUMENTS

| WO | WO 2007117272 A2 * | 10/2007 |
|---|---|---|
| WO | WO2010/126635 | 11/2010 |

OTHER PUBLICATIONS

Tsukamoto et al., (Injury, Int. J. Care Injured. Jan. 2010;41;21-26).*
Tanaka (Nihon Hoigaku Zasshi. Sep. 2004;58(2):130-40; Abstract only).*
Hauser et al., (Shock. Nov. 1998;10(5):324-8, Abstract only).*
Hauser et al., (Shock. Dec. 1999;12(6):428-37, Abstract only).*
Welborn et al., (Shock. Jul. 2003;20(1):35-40).*
Carson, (J Biol Chem. Jan. 15, 1987;262(2):718-21).*
Rappaport, (West J Med. Feb. 1993;158(2):153-61. Review).*
Akkose et al., "Relationships Between Markers of Inflammation, Severity of Injury, and Clinical Outcomes in Hemorrhagic Shock," *Advances in Therapy*, vol. 24, No. 5, pp. 955-962, Sep./Oct. 2007.
Al-amran et al., "Acute Lung Injury following Hemorrhagic Shock is governed by macrophage related factors that acts through neutrophils infiltration in a Hemorrhagic Shock rat model," Kufa Med.Journal, 14(2):71-77 (2011).
Daissormont, Issabelle, "Gut barrier dysfunction after hemorrhagic shock," Universiteit Hasselt, p. 1-51 uhdspace.uhasselt.be/dspace/handle/1942/1943 (2007).
Derikx et al., "New Insight in Loss of Gut Barrier During Major Non-Abdominal Surgery," *PLOSone*, vol. 3, p. 1-7, 2008.
European Search Report; Application No. 10770082.5-2404 / 2394174; mailed Jun. 29, 2012; Applicant: The General Hospital Corporation; 6 pages.
Final Office Action issued in U.S. Appl. No. 12/701,176 on Jun. 6, 2013 (9 pages).
International Search Report and Written Opinion, Application No. PCT/US2010/023342; Applicant: The General Hospital Corporation et al., mailing date: Dec. 21, 2010 (9 pages).
Kaiser et al., "Albumin Peptide: A Molecular Marker for Trauma/Hemorrhagic-Shock in Rat Mesenteric Lymph," *Peptides*, vol. 26, No. 12, pp. 2491-2499, Dec. 2005.
Li et al., "Cell protective mechanism of valproic acid in lethal hemorrhagic shock," Surgery, 144:217-24 (2008).
Li et al., "Effect of n-3 polyunsaturated fatty acids on membrane microdomain localization of tight junction proteins in experimental colitis," FEBS J., 275(3):411-420 (2008).
Li et al., "Identification of a Novel Potential Biomarker in a Model of Hemorrhagic Shock and Valproic Acid Treatment," *Journal of Surgical Research*, vol. 159, No. 1, pp. 474-481, Epub May 13, 2009.
Lomas-neira et al., "In vivo gene silencing (with siRNA) of pulmonary expression of MIP-2 versus KC results in divergent effects on hemorrhage-induced, neutrophil-mediated septic acute lung injury," Journal of Leukocyte Biology, 77(6):846-853 (Jun. 2005).
Non-Final Office Action issued in U.S. Appl. No. 12/701,176 on Sep. 5, 2012 (6 pages).
Paccione, "Cytokine and Chemokine Profiles in a Rat Model of Hemorrhagic Shock after Immuno-Modulation by Androstenetriol," Thesis, Jun. 13, 2008.
RCE and Response to Final Office Action issued in U.S. Appl. No. 12/701,176 on Jun. 6, 2013 filed on Dec. 6, 2013 (70 pages).
Response to Non-Final Office Action issued in U.S. Appl. No. 12/701,176 on Sep. 5, 2012 filed on Jan. 29, 2013 (8 pages).
Response to Restriction Requirement issued in U.S. Appl. No. 12/701,176 on May 25, 2012 filed on Jun. 8, 2012 (1 page).
Restriction Requirement issued in U.S. Appl. No. 12/701,176 on May 25, 2012 (6 pages).
Rinka et al., "Hemorrhagic Shock and Encephalopathy Syndrome—The Markers for an Early HSES Diagnosis," *BMC Pediatric*, vol. 8, No. 43, pp. 1-8, Oct. 16, 2008.
Shults et al., "Surviving blood loss without fluid resuscitation," J. Trauma, 64(3):629-638 (2008).
Thuijls et al., "Intestinal Cytoskeleton Degradation Precedes Tight Junction Loss Following Hemorrhagic Shock," Shock 31:164-169, 2008.
Thuijls et al., "Urine-based detection of Intestinal Tight Junction Loss," Medline Database; US National Library of Medicine; accession No. NLM19525861; Jan. 2010; 2 pages.
Wilson et al., "Diagnosis and Monitoring of Hemorrhagic Shock During the Initial Resuscitation of Multiple Trauma Patients: A Review," Journal of Emergency Medicine 24:413-422, 2003.
International Search Report and Written Opinion mailed Feb. 8, 2012 issued in international application No. PCT/US2011/036067, 8 pages.
Li et al., "Identification of a Novel Potential Biomarker in a Model of Hemorrhagic Shock and Valproic Acid Treatment," J. Surgical Research 159:474-481, 2010.
Rinka et al., "Hemorrhagic shock and encephalopathy syndrome—the markers for an early HSES diagnosis," BMC Pediatrics 8:43-50, 2008.
Kaiser et al., "Albumin peptide: A molecular marker for trauma/hemorrhagic-shock in rat mesenteric lymph," Peptide 26:2491-2499, 2005.

* cited by examiner

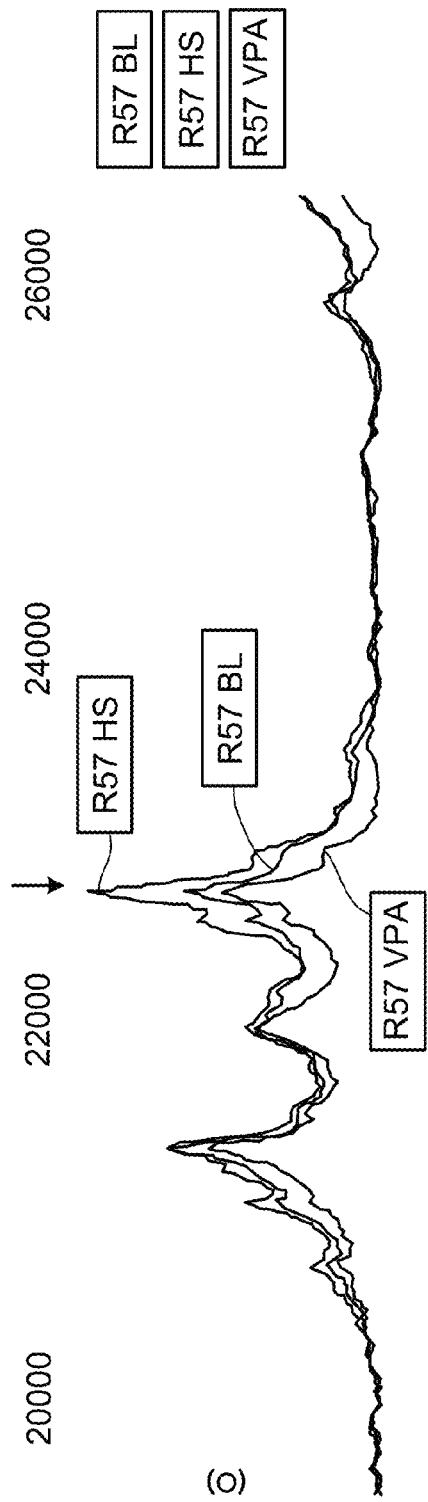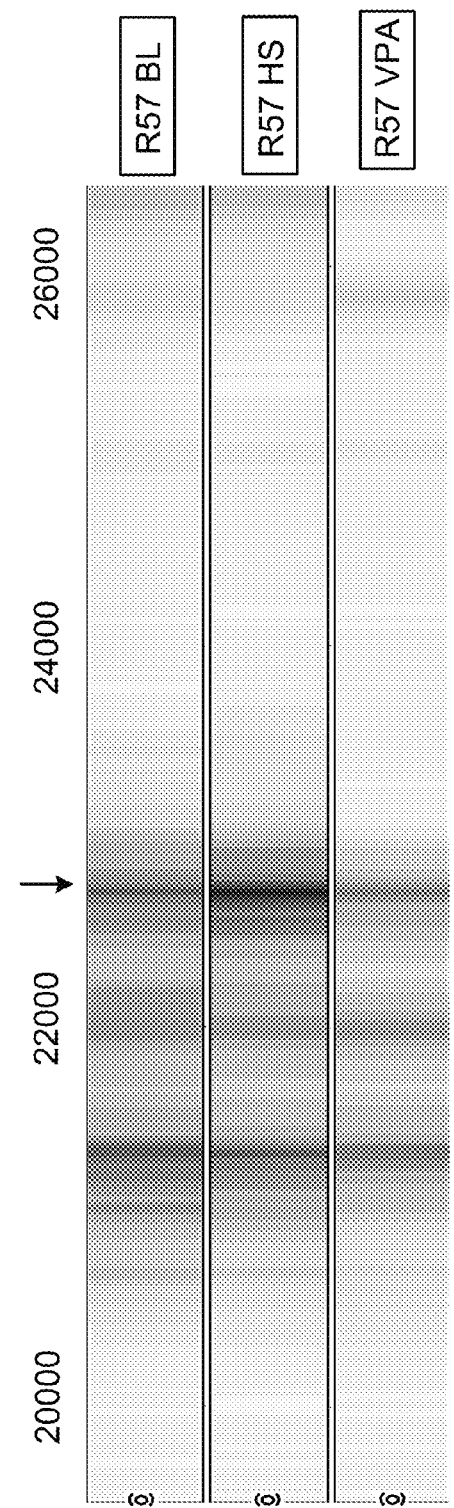

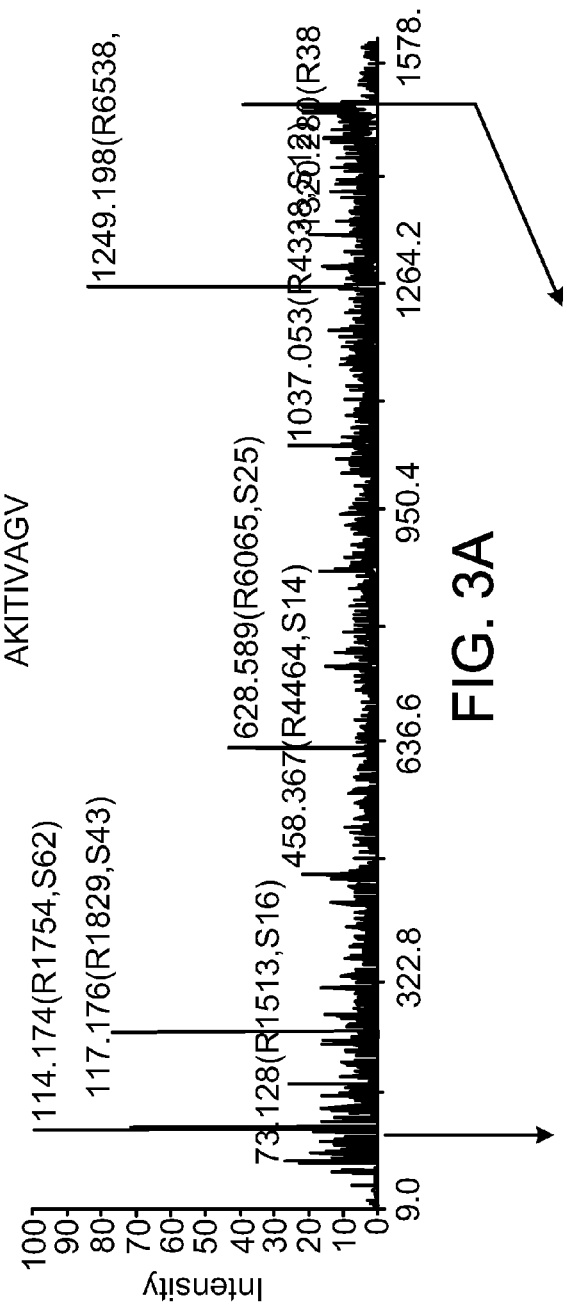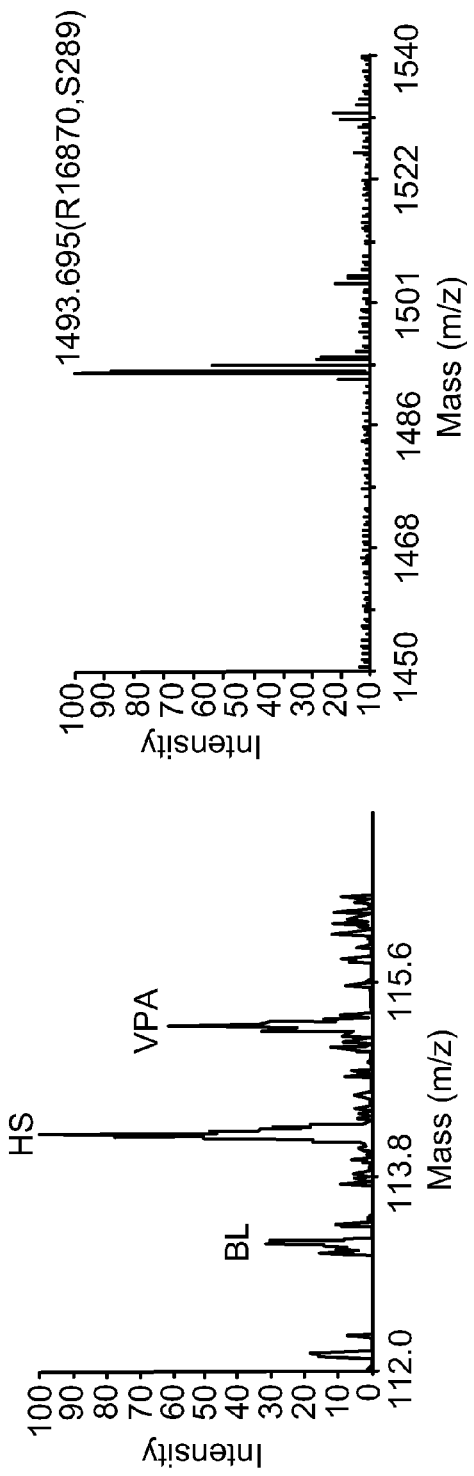
FIG. 3A
FIG. 3B
FIG. 3C

FIG. 4A
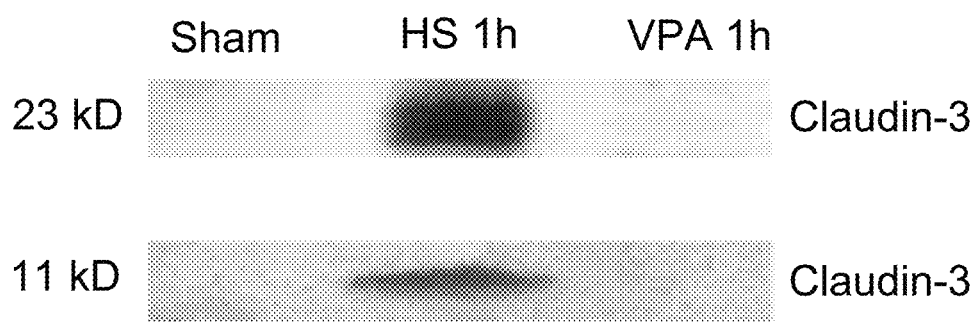
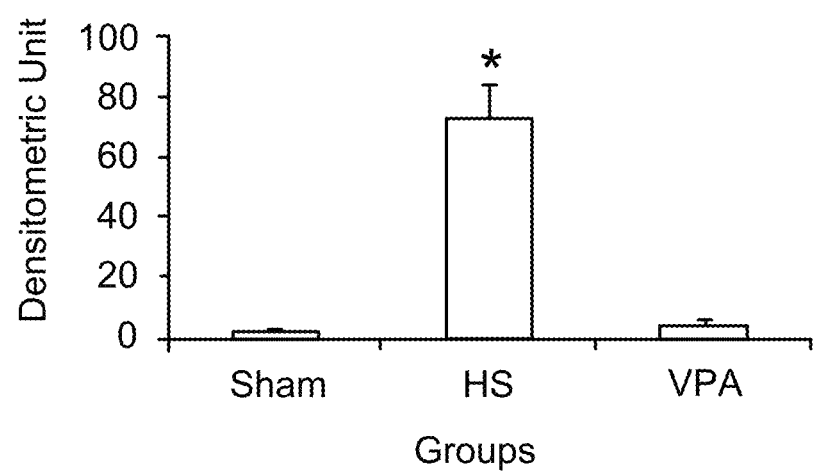
FIG. 4B

FIG. 5A
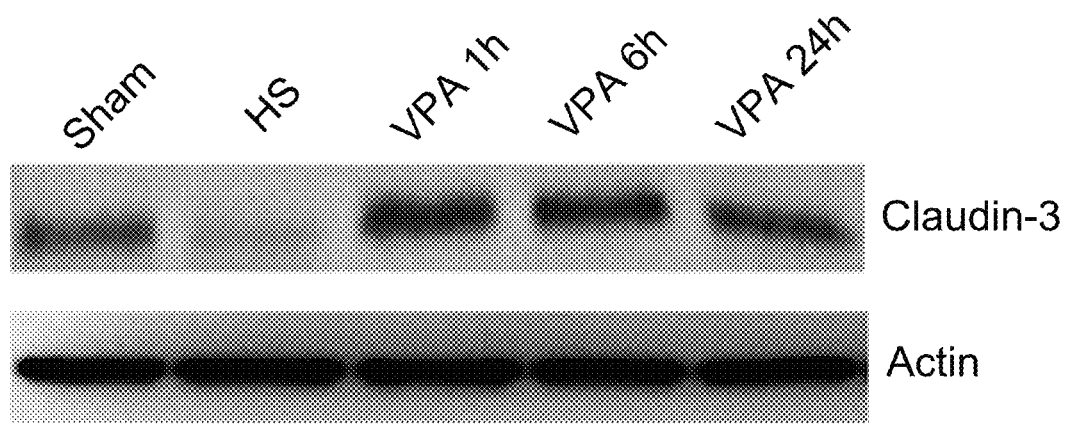
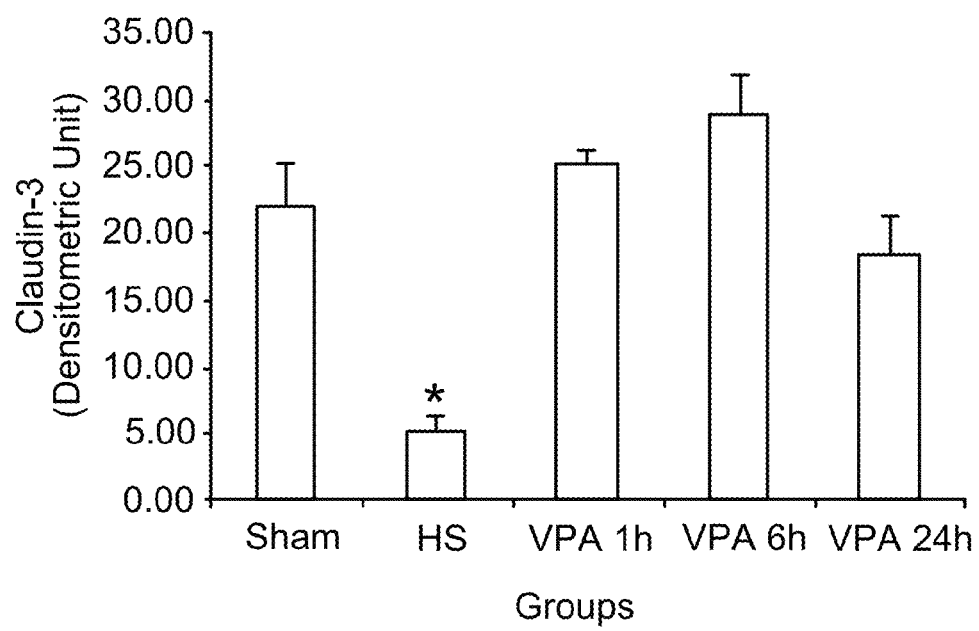
FIG. 5B

FIG. 6A
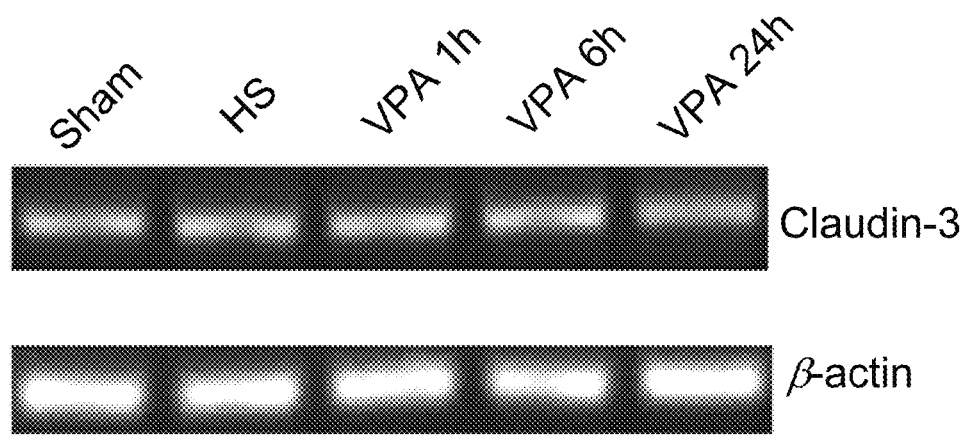
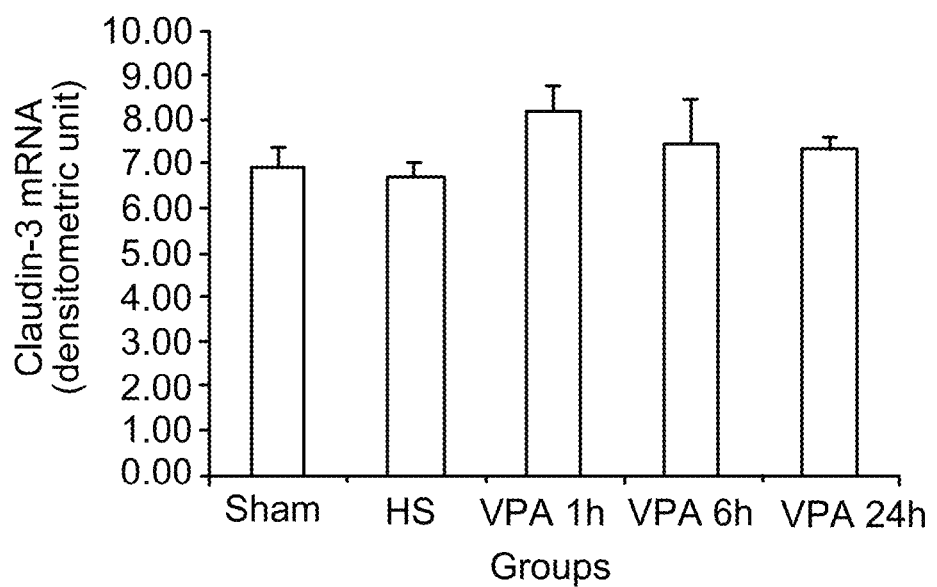
FIG. 6B

BIOMARKERS OF HEMORRHAGIC SHOCK

CROSS REFERENCE TO RELATED APPLICATIONS

This application is a U.S. National Phase Application under 35 U.S.C. 371 of International Application No. PCT/US2011/036067, filed on May 11, 2011, which claims priority from U.S. Provisional Application Ser. No. 61/333,475, filed on May 11, 2010, all of which are incorporated herein by reference in their entireties.

FEDERALLY SPONSORED RESEARCH OR DEVELOPMENT

This invention was made with Government support under Grant Nos. W81XWH-07-2-0011 from the Center for Integration of Medicine and Innovative Technology (CIMIT), W911NF-06-1-0220 awarded by the Defense Advanced Research Projects Agency (DARPA), and R01GM084127-01A1 awarded by the National Institutes of Health. The Government has certain rights in this invention.

TECHNICAL FIELD

The present invention relates generally to the field of biomarkers and trauma and more specifically to the use of biomarkers for diagnosis, prognosis, and therapeutics in hemorrhagic shock (HS) and treatment of HS.

BACKGROUND

Proteins that are found in the serum under normal circumstances may be increased in the presence of pathologic processes, and may return to normal levels following effective therapy. Cellular proteins may also "leak" into the circulation during pathologic processes. Because blood samples are easily obtained and processed, identification of serum biomarkers that accurately reflect the disease process is potentially very useful. While serum biomarkers have proven their utility in the diagnosis, prognosis and management of certain cancers, brain injury, and inflammatory disease, the use of biomarkers in diagnosing the pathological consequences or progression of traumatic hemorrhagic shock is only beginning to be explored.

Valproic acid (VPA), a well-known antiepileptic drug, has been shown to directly inhibit activity of histone deacetylase and induce hyperacetylation of both histone and non-histone proteins. Recently, it was demonstrated that VPA enhances acetylation of some histone and non-histone proteins, and improves survival after lethal HS in rats (Shults et al., J Trauma 64(3):629-638, 2008; Li et al., Surgery 144:217-24, 2008; WO 2007117272). However, it is not entirely clear how VPA affects hemorrhagic shock and whether any potential biomarkers of hemorrhagic shock are affected by the VPA treatment.

SUMMARY

The present invention is based, at least in part, on the identification by proteomic analysis of keratinocyte chemoattractant (KC)/human growth-regulated oncogene (GRO) (KC/GRO), apolipoprotein A2 (APOA2), angiotensinogen r (AGT), thyroglobulin (TG), disintegrin and metalloproteinase domain-containing protein 17 (ADAM17), anionic trypsin-1 (PRSS1), complement C4 (C4A), zona pellucida sperm-binding protein 1 (ZP1), neuropilin-2 (NRP2), solute carrier family 13 member 2 (SLC13A2), glucagon-like peptide 2 receptor (GLP2R), lipoma high mobility group protein isoform I-C (HMGIC) fusion partner-like protein 4 (LHFPL4), and claudin-3 (CLDN3) as biomarkers for the diagnosis and prognosis of HS, and as a measure of the efficacy of treatment of HS, e.g., VPA treatment of HS.

Thus, in one aspect, the invention provides methods for predicting the prognosis of a subject suffering from HS. The methods include obtaining a sample comprising serum from the subject; determining a level of one or more (e.g., two, three, four, five, six, seven, eight, nine, ten, eleven, or all) of KC/GRO, APOA2, AGT, TG, ADAM17, PRSS1, C4A, ZP1, NRP2, SLC13A2, GLP2R, and LHFPL4 in the sample to obtain a test value; and comparing the test value to a reference value. A comparison of the test value to the reference value indicates the subject's prognosis. The prognosis can be good (a good likelihood of recovery) or bad (a low likelihood of recovery or high likelihood of mortality, e.g., in the absence of an effective treatment) depending upon the comparison of the test value to the reference value. For example, if the reference value represents a threshold level of KC/GRO, APOA2, ADAM17, PRSS1, C4A, ZP1, NRP2, SLC13A2, GLP2R, or LHFPL4 then the presence of a level of KC/GRO, APOA2, ADAM17, PRSS1, C4A, ZP1, NRP2, SLC13A2, GLP2R, or LHFPL4 in the subject that is above its reference value indicates that the subject has an increased risk of mortality due to the HS, and the presence of a level of KC/GRO, APOA2, ADAM17, PRSS1, C4A, ZP1, NRP2, SLC13A2, GLP2R, or LHFPL4 in the subject that is below its reference value indicates that the subject has an increased chance of survival. If the reference value represents a threshold level of AGT or TG, then the presence of a level of AGT or TG in the subject that is below its reference value indicates that the subject has an increased risk of mortality due to the HS, and the presence of a level of AGT or TG in the subject that is above its reference value indicates that the subject has an increased chance of survival.

The methods can also include obtaining subsequent test values, e.g., taken at later time points, and evaluating the trend in the test values to determine a prognosis. For example, if the test value of KC/GRO, APOA2, ADAM17, PRSS1, C4A, ZP1, NRP2, SLC13A2, GLP2R, or LHFPL4 increases or does not change, or the test value of AGT or TG decreases or does not change, the prognosis would be bad (e.g., a failure to respond to treatment, and/or a likelihood of mortality and/or disability/morbidity), whereas a rapid (e.g., within 120, 90, 60, or 30 minutes of the first level, or of initiating a treatment) response (i.e., a decrease in KC/GRO, APOA2, ADAM17, PRSS1, C4A, ZP1, NRP2, SLC13A2, GLP2R, or LHFPL4 levels or an increase in AGT or TG levels), would suggest good prognosis.

In another aspect, the invention features methods for evaluating the efficacy of a treatment for HS in a subject, e.g., a mammal, e.g., a human. The methods include obtaining a first sample comprising serum, e.g., whole blood, plasma, or, serum from the subject; determining a level of one or more (e.g., two, three, four, five, six, seven, eight, nine, ten, eleven, or all) of KC/GRO, APOA2, AGT, TG, ADAM17, PRSS1, C4A, ZP1, NRP2, SLC13A2, GLP2R, and LHFPL4, in the first sample to obtain a first value, e.g., a pretreatment or baseline value; concurrently or subsequently administering a treatment for HS to the subject; obtaining a second or further sample comprising blood, e.g., whole blood, plasma, or serum, from the subject; determining a level of one or more (e.g., two, three, four, five, six, seven, eight, nine, ten, eleven, or all) of KC/GRO, APOA2, AGT, TG, ADAM17, PRSS1, C4A, ZP1, NRP2, SLC13A2, GLP2R, and LHFPL4 in the second sample to obtain a treatment value; and comparing the first value to its respective treatment value. A treatment value for KC/GRO, APOA2, ADAM17, PRSS1, C4A, ZP1, NRP2, SLC13A2, GLP2R, or LHFPL4 that is below its baseline value, a treatment value for AGT or TG that is above its baseline value, or a treatment value that comes back to or approaches its "normal" value or the baseline range indicates that the treatment is effective. In some embodiments, the first and second samples are or include serum. In some embodiments, the methods include obtaining further samples, and determining the levels of one or more (e.g., two, three, four, five, six, seven, eight, nine, ten, eleven, or all) of KC/GRO, APOA2, AGT, TG, ADAM17, PRSS1, C4A, ZP1, NRP2, SLC13A2, GLP2R, and LHFPL4 in the subsequent samples, wherein a decrease in the level of KC/GRO, APOA2, ADAM17, PRSS1, C4A, ZP1, NRP2, SLC13A2, GLP2R, or LHFPL4, or an increase in the level of AGT or TG, over time indicates that the treatment is working. In some embodiments, the treatment includes one or more of an effective amount of valproic acid (VPA), fluid resuscitation, or the transfusion of blood or blood products.

Also provided are methods of determining an effect of a treatment for HS on prognosis in a subject, e.g., a mammal, e.g., a human. The methods include obtaining a first sample comprising serum from the subject; determining a level of one or more (e.g., two, three, four, five, six, seven, eight, nine, ten, eleven, or all) of KC/GRO, APOA2, AGT, TG, ADAM17, PRSS1, C4A, ZP1, NRP2, SLC13A2, GLP2R, and LHFPL4 in the first sample to obtain a first value; administering a treatment for HS to the subject; obtaining a subsequent sample at a later time comprising serum from the subject; determining a level of one or more (e.g., two, three, four, five, six, seven, eight, nine, ten, eleven, or all) of KC/GRO, APOA2, AGT, TG, ADAM17, PRSS1, C4A, ZP1, NRP2, SLC13A2, GLP2R, and LHFPL4 in the subsequent sample to obtain a treatment value; and comparing the first value to its respective treatment value. A decrease in the level of KC/GRO, APOA2, ADAM17, PRSS1, C4A, ZP1, NRP2, SLC13A2, GLP2R, or LHFPL4, or an increase in the level of AGT or TG, from the first value to its respective treatment value indicates that the treatment has improved the subject's prognosis, and an increase or no change in the level of KC/GRO, APOA2, ADAM17, PRSS1, C4A, ZP1, NRP2, SLC13A2, GLP2R, or LHFPL4, or a decrease or no change in the level of AGT or TG, indicates that the treatment has not affected or has worsened the subject's prognosis. In some embodiments, the first and second samples comprise plasma or whole blood. In some embodiments, the treatment includes one or more of an effective amount of valproic acid (VPA), fluid resuscitation, or the transfusion of blood or blood products.

In a further aspect, the present invention features methods for diagnosing HS or determining a prognosis for HS in a subject, e.g., a mammal, e.g., a human. The methods include obtaining a sample comprising blood, e.g., whole blood, plasma, or serum, from the subject; determining a level of one or more (e.g., two, three, four, five, six, seven, eight, nine, ten, eleven, or all) of KC/GRO, APOA2, AGT, TG, ADAM17, PRSS1, C4A, ZP1, NRP2, SLC13A2, GLP2R, and LHFPL4 in the sample to obtain a test value; and comparing the test value to its reference value. A test value of KC/GRO, APOA2, ADAM17, PRSS1, C4A, ZP1, NRP2, SLC13A2, GLP2R, or LHFPL4 above its reference value or a test value of AGT or TG below its reference value indicates that the subject has HS, and/or has an increased risk of a negative outcome due to HS, e.g., mortality. In some embodiments, the reference value represents a level of one or more (e.g., two, three, four, five, six, seven, eight, nine, ten, eleven, or all) of KC/GRO, APOA2, AGT, TG, ADAM17, PRSS1, C4A, ZP1, NRP2, SLC13A2, GLP2R, and LHFPL4 in a subject who does not have HS, and/or does not have an increased risk of a negative outcome such as mortality.

In the methods described herein, serum levels of CLDN3 can also be used to diagnose HS and monitor treatment for HS, see, U.S. patent application Ser. No. 12/701,176. Therefore, CLDN3 can be used in combination with one or more (e.g., two, three, four, five, six, seven, eight, nine, ten, eleven, or all) of KC/GRO, APOA2, AGT, TG, ADAM17, PRSS1, C4A, ZP1, NRP2, SLC13A2, GLP2R, and LHFPL4.

In another aspect, the present invention features methods for diagnosing acute lung injury associated with HS in a subject, e.g., a mammal, e.g., a human, suffering from HS. The methods include obtaining a sample comprising blood, e.g., whole blood, plasma, or serum, from the subject; determining a level of KC/GRO in the sample to obtain a test value; and comparing the test value to a reference value. A comparison of the test value to the reference value indicates the subject's risk for acute lung injury. The diagnosis can be good (a low risk for acute lung injury) or bad (a high risk for acute lung injury) depending upon the comparison of the test value to the reference value. For example, if the level of KC/GRO in the subject is above the reference value, the subject has an increased risk for acute lung injury, and if the level of KC/GRO in the subject is below the reference value, the subject has a decreased risk for acute lung injury.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIGS. 1A and 1B are representative differential protein-profiling pattern (22.7 kDa indicated by arrow) in surface-enhanced laser desorption/ionization—time of flight mass spectrometry (SELDI-TOF MS) mass spectra (FIG. 1A) and respective gel views (FIG. 1B) of serum samples obtained at baseline (BL), following hemorrhagic shock (HS), and 24 hours after VPA treatment (VPA) from a single rat (No. R57).

FIG. 3A is a representative tandem mass spectrometry (MS/MS) sequence spectra used for sequence identification and quantification of a representative isobaric tag for relative and absolute quantitation (iTRAQ) labeled peptide. This spectra is for a single peptide mapping to claudin-3 protein (AKITIVAGV, SEQ ID NO:1).

FIG. 3B is an expanded m/z scale spectrum corresponding to the region containing the iTRAQ-tags used to determine the abundance of claudin-3 peptide in three serum samples. BL, baseline; HS, post-hemorrhagic shock; VPA, 24 hours post-VPA treatment.

FIG. 3C is a further expansion of the region showing the peptide parent ion that was sequenced and quantified.

FIGS. 4A and 4B are a Western blot (FIG. 4A) and bar graph (FIG. 4B) showing the results of validation analysis of claudin-3 in serum. Equal amounts of serum proteins from independent samples at BL, 1 hour of HS, and 1 hour following VPA treatment were separated on SDS-PAGE, transferred to nitrocellular membranes and probed with anti-claudin-3 antibody. Protein bands were quantified by densitometry and expressed as means±SEM (n=3). The symbol * indicates that a value significantly (p<0.05) differs from the other groups.

FIGS. 5A and 5B are a Western blot (FIG. 5A) and bar graph (FIG. 5B) showing levels of intestinal claudin-3 protein in hemorrhagic shock and VPA treatment. Equal amounts of intestinal tissue lysate from sham, HS, and 3 time-points following VPA treatment (VPA 1 hour, 6 hours and 24 hours) were subjected to SDS-PAGE and Western blotting with antibodies against claudin-3 and actin (internal control for equal loading). Specific protein bands were quantified by densitometry and expressed as means±SEM, n=3. The symbol * indicates that a value significantly (p<0.05) differs from the control group.

FIGS. 6A and 6B are a gel (FIG. 6A) and bar graph (FIG. 6B) showing levels of intestinal claudin-3 mRNA expression in HS and VPA treatment. Expression of claudin-3 mRNA was analyzed by RT-PCR with rat β-actin as an internal control. Specific gene bands were quantified by densitometry and expressed as means±SEM, n=3. No significant difference was found among the groups.

DETAILED DESCRIPTION

Figure 2:
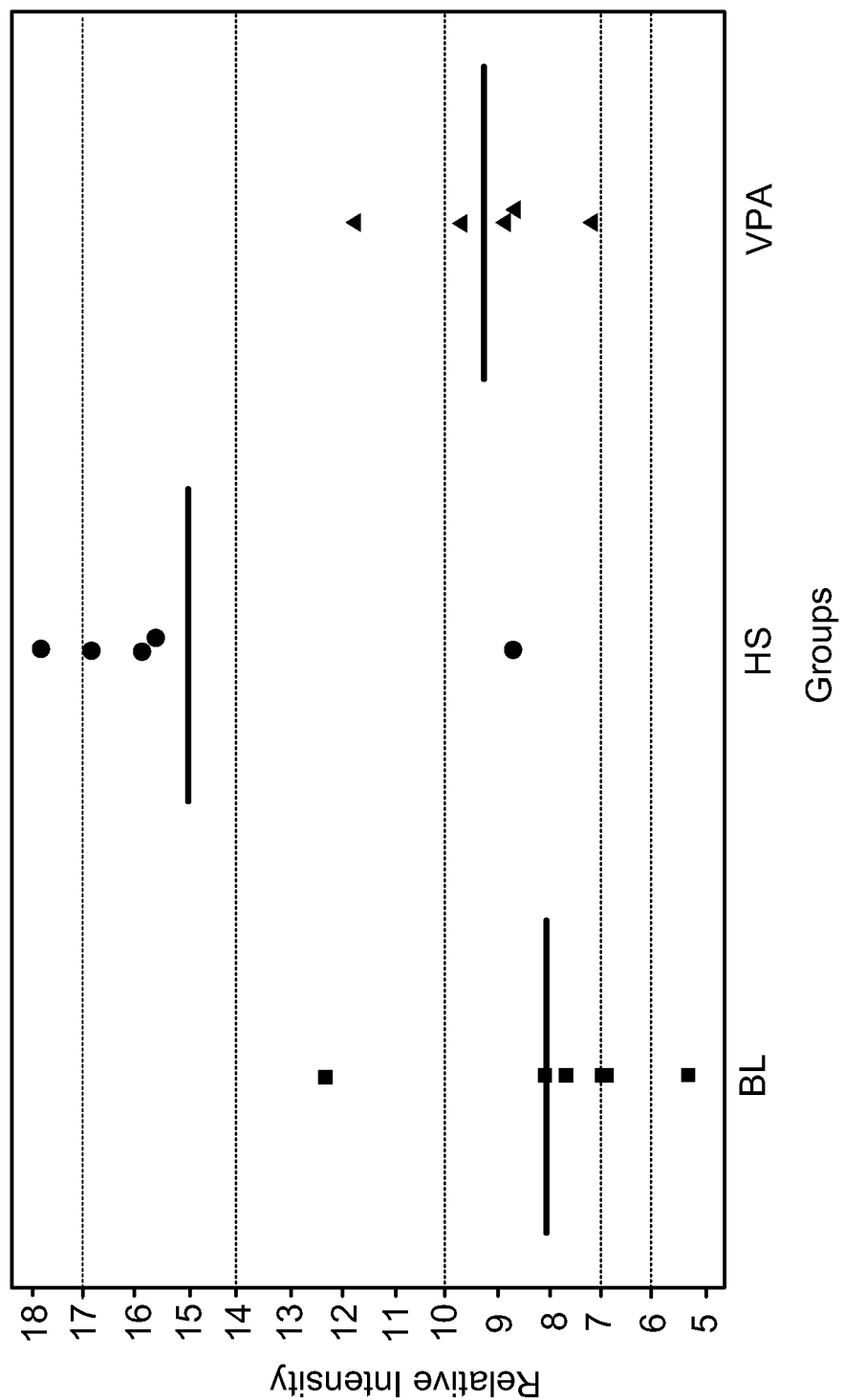
FIG. 2 is a dot graph showing serum levels of a 22.7 kDa protein at baseline (BL), following hemorrhagic shock (HS), and 24 hours after VPA treatment (VPA). The 22.7 kDa protein is increased in HS (middle) as compared to BL (left), and decreased in VPA (right) as compared to HS, in serum obtained from five animals (numbered R57, R106, T14, T58 and T59). The HS group significantly differs from those of the BL and VPA group (p<0.05). The bar (--) shows mean normalized intensity and the dots (•) are values of individual animals.

The initial management of a trauma patient often requires evaluation for potential hemorrhage and ongoing monitoring to assess the efficacy of treatment and avoid complications related to massive blood loss. As described herein, certain serum protein levels are altered in response to hemorrhagic shock, and thus serve as useful biomarkers to guide diagnosis, prognosis and therapeutics in traumatic hemorrhagic shock. Treatment with VPA has been shown to up-regulate various survival pathways and improve outcome (see, e.g., WO 2007117272).

Using surface-enhanced laser desorption/ionization (SELDI) mass spectrometry, the present inventors have demonstrated that HS alters levels of 13 proteins in the serum that is reversed by VPA treatment. Further iTRAQ studies showed that claudin-3, a 23 kDa protein, is elevated in the serum after HS, but VPA treatment decreases the serum claudin-3 protein levels back to normal. This finding was confirmed by Western blotting. In addition, HS causes claudin-3 protein loss in the intestine, and VPA treatment stabilizes the intestinal claudin-3 protein levels. These data indicate that claudin-3 is a potential biomarker for HS and drug treatment.

Biomarkers of Hemorrhagic Shock

Identification and quantification of iTRAQ-labeled peptides that mapped to 130 proteins (SwissProt) revealed 12 biomarkers whose serum levels were altered in early HS, and corrected by VPA treatment. These biomarkers include KC/GRO, APOA2, AGT, TG, ADAM17, PRSS1, C4A, ZP1, NRP2, SLC13A2, GLP2R, and LHFPL4 (Table 1). KC/GRO is a potent neutrophil chemokine APOA2 may stabilize HDL (high density lipoprotein) structure by its association with lipids and affect the HDL metabolism. AGT is a potent regulator of blood pressure, body fluid and electrolyte homeostasis. TG is a glycoprotein homodimer produced predominantly by the thyroid gland. ADAM17 is a transmembrane protein, and the exact function of the protein remains unclear but appears important for producing functionally efficient sperm. PRSS1 is a member of the trypsin family of serine proteases and has activity against the synthetic substrates Boc-Phe-Ser-Arg-Mec, Boc-Leu-Thr-Arg-Mec, Boc-Gln-Ala-Arg-Mec, and Boc-Val-Pro-Arg-Mec. C4A is a mediator of local inflammatory process. It induces the

TABLE 1

Biomarkers of hemorrhagic shock

| Biomarker | Nucleic Acid | Protein | GeneID | Antibody Sources |
|---|---|---|---|---|
| keratinocyte chemoattractant (KC)/human growth-regulated oncogene (GRO) | NM_001511.2 | NP_001502.1 | 2919 | R&D Systems (e.g., Cat. No. BAF275) |
| apolipoprotein A2 (APOA2) | NM_001643.1 | NP_001634.1 | 336 | Thermo Scientific (e.g., Cat. No. PA1-28972) |
| angiotensinogen r (AGT) | NM_000029.3 | NP_000020.1 | 183 | Immuno-Biological Laboratories Co. (e.g., Cat. No. 27412) |
| thyroglobulin (TG) | NM_003235.4 | NP_003226.4 | 7038 | Santa Cruz Biotechnology (e.g., Cat. No. sc-66090) |
| disintegrin and metalloproteinase domain-containing protein 17 (ADAM17) | NM_003183.4 | NP_003174.3 | 6868 | Abcam plc. (e.g., Cat. No. ab78162) |
| anionic trypsin-1 (PRSS1) | NM_002769.3 | NP_002760.1 | 5644 | Novus Biologicals (e.g., Cat. No. NBP1-30135) |
| complement C4 (C4A) | NM_007293.2 | NP_009224.2 | 720 | Assaypro (e.g., Cat. No. EC2102-1) |
| zona pellucida sperm-binding protein 1 (ZP1) | NM_207341.2 | NP_997224.2 | 22917 | Abcam plc. (e.g., Cat. No. ab90480) |
| Neuropilin-2 (NRP2) | NM_201266.1 | NP_957718.1 | 8828 | R&D Systems (e.g., Cat. No. MAB22151) |
| solute carrier family 13 member 2 (SLC13A2) | NM_001145975.1 | NP_001139447.1 | 9058 | Novus Biologicals (e.g., Cat. No. H00009058-A01) |
| glucagon-like peptide 2 receptor (GLP2R) | NM_004246.1 | NP_004237.1 | 9340 | Abcam plc. (e.g., Cat. No. ab56563) |
| lipoma HMGIC fusion partner-like protein 4 (LHFPL4) | NM_198560.2 | NP_940962.1 | 375323 | Santa Cruz Biotechnology (e.g., Cat. No. sc-99499) |
| claudin-3 (CLDN3) | NM_001306.3 | NP_001297.1 | 1365 | Abcam plc. (e.g., Cat. No. ab52231) | contraction of smooth muscle, increases vascular permeability and causes histamine release from mast cells and basophilic leukocytes. ZP1 ensures structural integrity of zona pellucida. NRP2 is a transmembrane protein and interacts with vascular endothelial growth factor. SLC13A2 is a sodium-dependent dicarboxylate transporter. GLP2R is a receptor for glucagon-like peptide 2. The activity of this receptor is mediated by G proteins which activate adenylyl cyclase. LHFPL4 is a member of the lipoma HMGIC fusion partner (LHFP) family, and the molecular function is unclassified. Hemorrhage resulted in a rapid increase in KC/GRO, APOA2, ADAM17, PRSS1, C4A, ZP1, NRP2, SLC13A2, GLP2R, and LHFPL4 levels and a rapid decrease in AGT and TG levels. VPA treatment corrects these alterations, and leads to improved survival. These biomarkers can be used to diagnose shock and monitor the effectiveness of a treatment.

The human sequences of KC/GRO, APOA2, AGT, TG, ADAM17, PRSS1, C4A, ZP1, NRP2, SLC13A2, GLP2R, and LHFPL4 are known in the art; exemplary reference sequences can be found in the GenBank database at the accession numbers shown in Table 1. Antibodies to each of the 12 proteins are commercially available, e.g., from Abcam plc.; Santa Cruz Biotechnology; R&D Systems; Acris Antibodies GmbH; Assaypro; Thermo Scientific; and Novus Biologicals.

Claudin-3 and Tight Junctions (TJ)

As described herein, VPA treatment attenuates shock-induced alteration of claudin-3 in both serum (increase) and intestine tissues (decrease). Moreover, the loss of claudin-3 in TJ is reversible during HS, as long as the animal is treated with VPA at an early stage. VPA is a histone deacetylase inhibitor (HDACI) which can induce acetylation of histone and non-histone proteins. It is unknown whether claudin-3 is directly acetylated, or whether acetylation of other proteins can affect claudin-3 stability within TJ. A recent study from Morin's group reported that claudin-3 expression is regulated through epigenetic processes. Cells that express high levels of claudin-3 exhibit high histone H3 acetylation of the critical claudin-3 promoter region. Claudin-3 negative cells can be induced to express claudin-3 through HDACI treatment (Honda et al., Cancer Biol Ther 2007; 6(11):1733-1742). It is conceivable that VPA treatment can also increase claudin-3 protein in TJ of intestinal cells via acetylation of histone H3 during HS.

Encircling epithelial and endothelial cells, TJ are a region where the plasma membrane of epithelial/endothelial cells forms a series of contacts that appear to completely occlude the extracellular space and create an intercellular barrier and intramembrane diffusion fence (Wong and Gumbiner, J Cell Biol 1997 136 (2):399-409). TJ serve as a fence dividing the cells into apical and basolateral domains and provide selective barriers in the intestine, blood-brain barrier, and other organs.

Claudin-3, a 23 kDa transmembrane protein, is essential for the formation and maintenance of TJ in epithelial and endothelial cells. The exact function of claudin-3 within a TJ is unclear, but it appears to be important in TJ formation and function. It has been found that intestinal inflammation causes damage to the mucosa which is accompanied by TJ structural disruption and alteration of claudin-3 expression (Li et al., FEBS J. 2008; 275(3):411-420). In a rodent model of hemorrhagic shock, loss of claudin-3 protein and TJ structure occur very early (Thuijls et al., Shock 2009; 31(2):164-169). This intestinal barrier loss results in translocation of toxins and bacteria. It is still unknown how claudin-3 is lost and where the protein goes. Recent studies have shown that hemorrhagic shock leads to destruction of the intestinal barrier due to TJ protein loss very early after the onset of shock (Thuijls et al., Shock 2009; 31(2):164-169).

There is growing evidence that remodeling of the apical junctional complex including adhesion junctions (AJ) and TJ is mediated by internalization of junctional proteins (Ivanov et al., BioEssays 2005; 27:356-365). However, little is known about whether claudin-3 is disassembled from TJ by endocytosis or an alternative mechanism. The data described herein suggest that claudin-3, at least in part, enters the circulation soon after HS. Cleavage of claudin-3 by protein proteases may occur during this process because two claudin-3 bands were detected in the serum by Western blot (FIG. 4).

The human sequence is known in the art; an exemplary reference sequence can be found in the GenBank database at accession number NM_001306.3 (nucleic acid) and NP_001297.1 (amino acid). See also GeneID: 1365. Claudin-3 antibodies are commercially available, e.g., from Abcam plc. (e.g., ab15102); Santa Cruz Biotechnology (e.g., sc-17662); Invitrogen (Cat. No. 34-1700); Acris Antibodies GmbH; and Novus Biologicals.

Diagnosing Hemorrhagic Shock

The methods described herein can be used to diagnose the presence of, and monitor the efficacy of a treatment for, hemorrhagic shock ("HS"). HS is shock brought on by a loss (e.g., an acute or chronic loss) of circulating blood volume and/or oxygen carrying capacity. HS can result from any condition associated with blood loss, e.g., internal (e.g., gastrointestinal bleeding) or external hemorrhage, and trauma (e.g., penetrating or blunt trauma), among others.

Hemorrhagic shock followed by resuscitation (HS/R) causes a systemic inflammatory response and often leads to organ injury and failure. The injury occurring following hemorrhagic shock is unique in that there is a global insult to all organ systems. The inability to meet the cellular metabolic demands results in rapid tissue injury and organ dysfunction.

Outward symptoms of HS include, e.g., reduced urine output (e.g., oliguria or anuria), delayed capillary refill, increased heart rate, cool and clammy skin, compromised mental status (e.g., confusion, agitation, or lethargy), weakness, and increased respiration rate. A skilled practitioner will appreciate that hemorrhagic shock can be caused by any factor or condition that results in a substantial loss of blood from a patient, e.g., trauma (e.g., penetrating or blunt trauma), surgery, childbirth, and internal/external hemorrhages. However, these typical signs and symptoms are seen in advanced stages of HS. Early diagnosis is often difficult, and use of sensitive biomarkers that can identify shock before it becomes clinically apparent can result in early administration of life saving therapies.

As demonstrated herein, hemorrhagic shock causes an acute rise in serum KC/GRO, APOA2, ADAM17, PRSS1, C4A, ZP1, NRP2, SLC13A2, GLP2R, LHFPL4, and CLDN3 protein levels, a decrease in serum AGT and TG protein levels, an increase in KC/GRO levels in lung tissue, and a decrease in intestinal claudin-3 expression. Further, VPA treatment attenuates these alterations and stabilizes intestinal claudin-3 levels. The results demonstrate that serum levels of KC/GRO, APOA2, AGT, TG, ADAM17, PRSS1, C4A, ZP1, NRP2, SLC13A2, GLP2R, and LHFPL4, and claudin-3 are biomarkers for HS and drug treatment of HS.

Individuals considered at risk for HS may benefit particularly from the methods described herein, primarily because once an elevated serum level of KC/GRO, APOA2, ADAM17, PRSS1, C4A, ZP1, NRP2, SLC13A2, GLP2R, LHFPL4, or claudin-3, or a decreased serum level of AGT or TG, is detected, e.g., in a subject who is at risk for HS, early treatment can begin before there is any clinical evidence of HS. Individuals "at risk" include, e.g., individuals suffering from any condition described above, or having another factor that may put a patient at risk for blood loss, e.g., a chronic or hereditary disorder (e.g., hemophilia). For example, a person suffering from a wound (e.g., blunt trauma, a stab wound, or surgery) or a gastrointestinal bleed that has not yet lost a volume of blood sufficient to cause HS, can be diagnosed according to the methods described herein and treated (e.g., with fluids and/or VPA) before HS occurs.

Skilled practitioners will appreciate that a patient can be identified as at risk for HS by any method known in the art, e.g., by a physician or other medical personnel.

In some embodiments, the methods of diagnosis described herein are performed in conjunction with a standard HS workup, e.g., including laboratory tests (e.g., complete blood count (CBC); prothrombin time and/or activated partial thromboplastin time; urine output rate; arterial blood gases (ABG) (levels reflect acid-base and perfusion status); and lactate and base deficit (used in some centers to indicate the degree of metabolic debt; clearance of these markers over time can reflect the adequacy of resuscitation). Imaging studies, e.g., (standard radiography, computed tomography, ultrasonography, and directed angiography), an ECG, or tissue oximetry can also be used.

Methods for diagnosing HS include determining a level of one or more (e.g., two, three, four, five, six, seven, eight, nine, ten, eleven, or all) of KC/GRO, APOA2, AGT, TG, ADAM17, PRSS1, C4A, ZP1, NRP2, SLC13A2, GLP2R, and LHFPL4 in the serum of the subject to obtain a KC/GRO, APOA2, AGT, TG, ADAM17, PRSS1, C4A, ZP1, NRP2, SLC13A2, GLP2R, or LHFPL4 value, and comparing the value to an appropriate reference value, e.g., a value that represents a threshold level, above which the subject can be diagnosed with HS. The reference can also be a range of values, e.g., that indicate severity of HS in the subject. A suitable reference value can be determined by methods known in the art, e.g., reference cohort of normal subjects or subjects with HS. A reference value can be a mean or median level of a biomarker of HS as described herein, or any other statistically significant cutoff.

Therefore, included herein are methods for diagnosing HS in a subject. The methods include obtaining a sample from a subject, and evaluating the presence and/or level of one or more of KC/GRO, APOA2, AGT, TG, ADAM17, PRSS1, C4A, ZP1, NRP2, SLC13A2, GLP2R, and LHFPL4 in the sample, and comparing the presence and/or level with one or more references, e.g., a control reference that represents a normal level of KC/GRO, APOA2, AGT, TG, ADAM17, PRSS1, C4A, ZP1, NRP2, SLC13A2, GLP2R, and LHFPL4, e.g., a level in an unaffected subject, and/or a disease reference that represents a level of KC/GRO, APOA2, AGT, TG, ADAM17, PRSS1, C4A, ZP1, NRP2, SLC13A2, GLP2R, and LHFPL4 associated with HS, e.g., a level in a subject having HS. The presence and/or level of a protein can be evaluated using methods known in the art, e.g., using quantitative immunoassay methods such as enzyme linked immunosorbent assays (ELISAs), immunoprecipitations, immunofluorescence, enzyme immunoassay (EIA), radioimmunoassay (RIA), and Western blot analysis. In some embodiments, the methods include contacting an agent that selectively binds to the KC/GRO, APOA2, AGT, TG, ADAM17, PRSS1, C4A, ZP1, NRP2, SLC13A2, GLP2R, and LHFPL4 protein (such as an antibody or antigen-binding portion thereof) with a sample, to evaluate the level of protein in the sample. In some embodiments, the antibody bears a detectable label. Antibodies can be polyclonal, or more preferably, monoclonal. An intact antibody, or an antigen-binding fragment thereof (e.g., Fab or F(ab')2) can be used. The term "labeled," with regard to an antibody encompasses direct labeling of the antibody by coupling (i.e., physically linking) a detectable substance to the antibody, as well as indirect labeling of the antibody by reactivity with a detectable substance. Examples of detectable substances are known in the art and include chemiluminescent, fluorescent, radioactive, or colorimetric labels. For example, detectable substances can include various enzymes, prosthetic groups, fluorescent materials, luminescent materials, bioluminescent materials, and radioactive materials. Examples of suitable enzymes include horseradish peroxidase, alkaline phosphatase, beta-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$, or $^{3}H$.

In some embodiments, high throughput methods, e.g., protein or gene chips as are known in the art (see, e.g., Ch. 12, "Genomics," in Griffiths et al., Eds. *Modern Genetic Analysis*, 1999, W. H. Freeman and Company; Ekins and Chu, Trends in Biotechnology 1999; 17:217-218; MacBeath and Schreiber, Science 2000, 289(5485):1760-1763; Simpson, Proteins and Proteomics: A Laboratory Manual, Cold Spring Harbor Laboratory Press; 2002; Hardiman, Microarrays Methods and Applications: Nuts & Bolts, DNA Press, 2003), can be used to detect the presence and/or level of KC/GRO, APOA2, AGT, TG, ADAM17, PRSS1, C4A, ZP1, NRP2, SLC13A2, GLP2R, and LHFPL4.

In some embodiments, microfluidic (e.g., "lab-on-a-chip") devices can be used in the present methods for detection and quantification of biomarkers of HS as described herein in a sample. Such devices have been successfully used for microfluidic flow cytometry, continuous size-based separation, and chromatographic separation. In particular, such devices can be used for the isolation of specific biological particles such as specific proteins (e.g., a biomarker of HS as described herein) from complex mixtures such as serum, plasma, or whole blood. A variety of approaches may be used to separate the biomarker proteins from a heterogeneous sample. For example, some techniques can use functionalized materials to capture the proteins using functionalized surfaces that bind to the target cell population. The functionalized materials can include surface-bound capture moieties such as antibodies or other specific binding molecules, such as aptamers, as are known in the art. Accordingly, such microfluidic chip technology may be used in diagnostic and prognostic devices for use in the methods described herein. For examples, see, e.g., Lion et al., Electrophoresis 24(21):3533-3562 (2003); Fortier et al., Anal. Chem. 77(6):1631-1640 (2005); U.S. Patent Publication No. 2009/0082552; and U.S. Pat. No. 7,611,834. Also included in the present application are microfluidics devices comprising binding moieties, e.g., antibodies or antigen-binding fragments thereof that bind specifically to the biomarkers of HS as described herein.

In some embodiments, the presence and/or level of the biomarker proteins is comparable to the presence and/or level of the protein(s) in a disease reference, and the subject has one or more symptoms associated with HS, then the subject has HS. In some embodiments, the subject has no overt signs or symptoms of HS, but the presence and/or level of one or more of the proteins evaluated is comparable to the presence and/or level of the protein(s) in the disease reference, then the subject has an increased risk of developing HS. In some embodiments of the present methods, the sample is or includes blood, plasma, and/or serum, or a portion or subfraction thereof. In some embodiments, the sample is or includes urine or a portion or subfraction thereof. In some embodiments, once it has been determined that a person has HS, or has an increased risk of developing HS, then a treatment, e.g., as known in the art or as described herein, can be administered. The efficacy of the treatment can be monitored using the methods described herein.

Monitoring the Efficacy of Treatments of HS

The methods described herein can include using serum levels of one or more biomarkers of HS as described herein to monitor the effectiveness of a treatment for HS, e.g., the administration of an effective amount of a pharmaceutical agent for the treatment of HS. The terms "effective amount" and "effective to treat," as used herein, refer to an amount that is effective within the context of its administration for causing an intended effect or physiological outcome. Effective amounts in the present context include, for example, amounts that reduce injury to a specific organ(s) effected by HS, or generally improve the patient's prognosis following HS. The term "treat(ment)" is used herein to describe delaying the onset of, inhibiting, or alleviating the detrimental effects of a condition, e.g., organ injury/failure associated with or caused by HS. A standard treatment for hemorrhagic shock is fluid resuscitation and the transfusion of blood and/or blood products. Other treatments include the administration of VPA (see, e.g., WO 2007117272; Li et al., Surgery 2008 August; 144(2):217-224; Li et al., J. Surg. Res. 2008; 144(2):261-262); other HDAC1 inhibitors (see, e.g., WO 2006060382, WO 2006117165, WO 2004063169, and WO 2004071401); or carbon monoxide (see, e.g., U.S. 2004-0228930). In some embodiments, the treatment includes the administration of vasopressors, e.g., dopamine, norepinephrine, Vasopressin (Pitressin), epinephrine (adrenaline, Bronitin). See, e.g., Cocchi et al., Emerg Med Clin North Am. August 2007; 25(3):623-642, vii; Gutierrez et al., Crit Care. October 2004; 8(5):373-381; Bickell et al., N Engl J Med. 331(17):1105-1109.

The methods described herein can be used to monitor the efficacy of a treatment for HS. For example, multiple serum levels of one or more biomarkers of HS as described herein can be determined over time, and the change in levels is indicative of whether the treatment is effective: a decrease in one or more of KC/GRO, APOA2, ADAM17, PRSS1, C4A, ZP1, NRP2, SLC13A2, GLP2R, LHFPL4, and claudin-3 serum levels over time indicates that the treatment is effective, while no change or an increase indicates that the treatment is not effective. An increase in one or more of AGT and TG serum levels over time indicates that the treatment is effective, while no change or a decrease indicates that the treatment is not effective.

Kits

The invention also includes kits for detecting the presence of one or more of KC/GRO, APOA2, AGT, TG, ADAM17, PRSS1, C4A, ZP1, NRP2, SLC13A2, GLP2R, LHFPL4, and Claudin-3 in a biological sample. For example, the kit can include a compound or agent capable of detecting one or more of KC/GRO, APOA2, AGT, TG, ADAM17, PRSS1, C4A, ZP1, NRP2, SLC13A2, GLP2R, LHFPL4, and Claudin-3 protein or mRNA in a biological sample; and a standard. The compound or agent can be packaged in a suitable container. The kit can further comprise instructions for using the kit to detect one or more of KC/GRO, APOA2, AGT, TG, ADAM17, PRSS1, C4A, ZP1, NRP2, SLC13A2, GLP2R, LHFPL4, and Claudin-3 protein or nucleic acid.

For antibody-based kits, the kit can include: (1) a first antibody (e.g., attached to a solid support) which binds to a polypeptide corresponding to a marker of the invention; and, optionally, (2) a second, different antibody which binds to either the polypeptide or the first antibody and is conjugated to a detectable agent.

For oligonucleotide-based kits, the kit can include: (1) an oligonucleotide, e.g., a detectably labeled oligonucleotide, which hybridizes to a nucleic acid sequence encoding a polypeptide corresponding to a marker of the invention or (2) a pair of primers useful for amplifying a nucleic acid molecule corresponding to a marker of the invention. The kit can also include a buffering agent, a preservative, or a protein stabilizing agent. The kit can also include components necessary for detecting the detectable agent (e.g., an enzyme or a substrate). The kit can also contain a control sample or a series of control samples which can be assayed and compared to the test sample contained. Each component of the kit can be enclosed within an individual container and all of the various containers can be within a single package, along with instructions for interpreting the results of the assays performed using the kit.

The methods described herein may be performed, for example, by utilizing pre-packaged diagnostic kits comprising at least one probe nucleic acid or antibody reagent described herein, which may be conveniently used, e.g., in clinical settings to diagnose patients exhibiting symptoms or family history of a disease or illness involving one or more of KC/GRO, APOA2, AGT, TG, ADAM17, PRSS1, C4A, ZP1, NRP2, SLC13A2, GLP2R, LHFPL4, and Claudin-3 genes.

EXAMPLES

The invention is further described in the following examples, which do not limit the scope of the invention described in the claims.

Example 1

Mass Spectrometric Data Obtained from Serum Samples Reveal Differentially Elevated Proteins in the Circulation VPA treatment increases acetylation of histone and non-histone proteins, protects cells from apoptosis, and improves animal survival after HS (Li et al., Surgery 144:217-224, 2008). In the present study, modern proteomic techniques were used to study changes in serum protein levels during HS and treatment of HS with VPA.

An animal model of HS was used. Male Wistar-Kyoto rats (254.12±2.71 grams, Harlan, Indianapolis, Ind.) were used in the lethal model of hemorrhagic shock (Shults et al., J Trauma 2008; 64(3):629-638). Each animal's estimated blood volume was calculated using the formula: [estimated blood volume (mL)=weight (g)×0.06 (mL/g)+0.77]. About 1.3 mL of blood was manually drawn at the beginning and end of hemorrhage for analysis (included in the total hemorrhage calculation). The animals were hemorrhaged (40% of their calculated total blood volume) via a femoral arterial catheter over 10 minutes, followed by a 20% blood volume venous bleed over the next 50 minutes. Bleeding was performed using Kent Scientific adjustable pumps (Kent Scientific Corporation, N.J.). VPA (300 mg/kg) was administered via a femoral vein catheter after completion of hemorrhage. Blood pressure was monitored continuously during the experiment. The mean arterial pressure (MAP) in animals that were subjected to hemorrhage dropped sharply after bleeding to approximately 20 mm Hg. Blood was drawn at baseline (BL, before hemorrhage), hemorrhagic shock (HS), and 24 hours after VPA treatment from individual rats for protein biomarker screening and identification. Blood was drawn from an independent group of rats: sham (instrumentation control), HS without treatment (1 hours after hemorrhagic shock) and VPA treatment (1 hour after treatment), and was used for validation of the protein biomarker. Serum was immediately prepared from the blood and stored in aliquots at −80° C. prior to proteomic analysis. Intestine was harvested from an independent group of animals: sham, HS without treatment (1 hour after HS), and 1 hour, 6 hours and 24 hours following VPA treatment. The tissues were further homogenized and extracted using Whole Cell Extraction Kit (Chemicon International, Temecula, Calif.) for biomarker analysis by Western blot.

To screen for potential biomarkers of hemorrhagic shock and treatment, serum samples at BL, HS and VPA treatment were subjected to CH10 protein chip analysis using SELDI-TOF MS.

ProteinChip profiling was performed on CM10 ProteinChip arrays (Ciphergen Biosystems, Fremont Calif.), as recommended by the manufacturer. Arrays were processed in an automated fashion on a dedicated Biomek 2000 robotic station (Beckman Coulter). Briefly, 20 µl of serum was diluted with 30 µl of U9 buffer (Ciphergen Expression Difference Mapping Kit for Serum Fractionation), incubated for 30 minutes on ice and then further diluted ⅒ with binding buffer containing 10% acetonitrile (ACN), 0.1% TFA vs. 20% ACN, 0.1% TFA, and applied to the ProteinChip arrays. The arrays were equilibrated by two washes with 100 µl of binding buffer, and then had 95 µl of binding buffer added followed by 5 µl of the various denatured sera. The samples were incubated for 1 hour on a MicroMix shaker (American Laboratory Trading LLC, Groton, Conn.). The arrays were washed with 150 µl aliquots of binding buffer three times and 200 µl of water twice. Finally 2×1 µl aliquots of SPA matrix (50% saturation, prepared in 50% ACN, 0.5% TFA) was added to each spot. The arrays were then inserted into a ProteinChip (Enterprise edition) TOF-MS and read at an optimized laser setting of 2000 nJ-5000 nJ. Each sample was profiled in duplicate. In addition, pooled serum samples were made by combining 3 µl aliquots of the individual samples. The pooled denatured sera were profiled in quadruplicate to assess reproducibility and performance.

For data analysis, SELDI ProteinChip Data Manager software was utilized. Spectra, profiled on CM10 ProteinChip, using a specific buffer and identical laser settings were normalized relative to the total ion current across the spectra. Calibration was performed using All-in-1 peptide and All-in-1 protein standards (Ciphergen Biosystems). Spectra were then aligned using a reference sample spectrum. Univariate analysis was carried out to indicate specific mass/charge (m/z) markers which showed differential expression across the three groups. Duplicate spectra obtained for each of the individual samples were averaged, so that each group contained n=5 independent samples. Peak reported to have significant (p<0.05) differences in expression were individually examined for peak quality.

The CH10 surface yielded the most readily discernable mass/charge (m/z) peaks that were distinguishable above background. One of the best resolution m/z peaks was observed at 22.7 kDa. As shown in FIGS. 1A and 1B, the 22.7 kDa protein was up-regulated in the HS group and down-regulated in the VPA group sharply. The results indicate that HS and VPA treatment markedly affect the serum level a protein with a molecular weight of 27 kDa.

To ensure that the data was reliable, serum samples of BL, HS and VPA treatment were collected from five animals and profiled on CH10 chips. The patterns obtained were reproducible, and common features were identifiable among all the samples. The peak intensity of the differentially expressed 22.7 kDa protein in all 5 samples is shown in the scatter plot (FIG. 2; significant differences between BL and HS, HS and VPA treatment, p<0.05).

Statistical significance of differences between groups for all the analyses described herein was determined using one-way ANOVA followed by Dunnett's multiple compari-

Example 2

Sequence Identification and Quantification of iTRAQ-Labeled Peptides

Proteome analysis using iTRAQ reagents compares favorably with other proteomic approaches for protein identification. Although it is low throughput (four samples per run), time consuming, and sample intensive, iTRAQ methods can be used to identify and quantify proteins across diverse MW and pI ranges. iTRAQ reagents also allow multiple, independent measures of protein abundance in the same experiment, enabling statistical estimates of protein quantitation (Aggarwal et al., Brief Funct Genomic Proteomic 2006; 5(2):112-120; Engwegen et al., Trends Pharmacol Sci 2006; 27(5):251-259). An improved signal-to-noise ratio with increased signal intensity in matrix assisted laser desorption/ionization time-of-flight (MALDI TOF)/TOF of isobarically tagged peptides cannot only result in detection of a greater number of peptides per protein with high confidence, but also in detection of some low-abundance proteins. To further identify potential biomarkers, serum samples were taken from rats R57 and T14 and used to perform an additional study using iTRAQ.

Immunodepletion of serum abundant proteins was performed as follows. Equal volumes of serum from rats (No. T14 and No. R57) at different time points (BL, HS and VPA treatment) were immunodepleted using ProteomeLab immunodepletion spin columns (Beckman Coulter, Fullerton, Calif.) to remove the top-7 proteins in overall abundance (albumin, immunoglobulin G, alpha 1-antitypsin, IgM, transferring, haptoglobin, and fibrinogen). Briefly, 10 µl of the serum was incubated with the immobilized antibodies in separate spin columns for each sample and processed in parallel. After the initial binding for 15 minutes at room temperature with agitation, each column was then centrifuged for 30 seconds at 500×g, and the immunodepleted flow-through was collected. Several rounds of depletion on fresh 10 µl aliquots were required in order to build up enough depleted protein. Column performance was monitored by sodium dodecyl sulphate-polyacrylamide gel electrophoresis (SDS-PAGE) followed by Coomassie Blue staining (BioBlue, BioRad). Removal of the most abundant protein, albumin, was employed as the visual measure of successful depletion based on comparison to undepleted serum. The flow-through from immunodepletion were pooled, precipitated with six volumes of acetone overnight at −20 C, pelleted, and saved at −80° C. for use.

iTRAQ labeling was performed as follows. Acetone-precipitated proteins (50 µg total depleted proteins from each sample) were reduced by incubation with TCEP and then free cysteine residues were blocked with MMTS. This was followed by overnight trypsin digestion. Digested peptides in each sample were labeled with their respective iTRAQ reagent (BL-113, HS-114, VPA-115 for rat No. T14 serum; BL-116, HS-117, VPA-117 for No. R57 rat serum) according to the manufacturer's protocol (Applied Biosystems, Foster City, Calif.). After completion of the labeling reaction, the six separate iTRAQ reaction mixtures were pooled into one sample, and partially purified by a combination of preparative strong cation exchange (SCX, POROS HS/20, Applied Biosystems) and reverse-phase (RP, C18 PepMap column, 75 um I.D. X, Dionex) chromatography to separate peptides in order to minimize the effects of ion suppression from the more abundant peptides. Collected fractions were pooled based on the SCX chromatogram so that fifteen fractions were run on RP chromatography. Nano-flow RP was performed on a Dionex instrument and samples were printed to AB4800 metal target plates using a ProBot spotter. CHCA was automatically added to eluted peptides in the ProBot mixing tee to a final concentration of 2.5 mg/ml. Peptides were identified using the ABI4800 Plus MALDI TOF/TOF instrument (Applied Biosystems). Peptide and protein identification as well as relative quantitation was determined by the Protein Pilot 2.0 software package (Applied Biosystems). Searches were performed against rat proteins in the SwissProt, Trembl, and NCBI non-redundant databases.

The rat R57 BL sample was labeled with iTRAQ-113, HS with iTRAQ-114 and VPA with iTRAQ-115. The rat T14 BL sample was labeled with iTRAQ-116, HS with iTRAQ-117 and VPA with iTRAQ-118. Duplicate LC-MS/MS were performed to identify proteins present in the serum and to quantify the ratios of the isobaric tags among the BL, HS and VPA samples. A MS/MS sequence from a representative peptide fragment is shown in FIG. 3A. MS/MS sequence spectra for a single peptide was mapped to claudin-3 protein. The intensity of the respective isobaric tag signals for this peptide, derived from their relative abundance in each group, is shown in FIG. 3B. The ratios of BL to HS and VPA to HS were 0.323 and 0.425, respectively. The parent ion peak (m/z=1493.695) for this peptide is shown in FIG. 3C. The results indicate that HS increases claudin-3 and VPA treatment decreases claudin-3 protein in the serum, suggesting that claudin-3 might serve as a potential biomarker of hemorrhagic shock and treatment.

Example 3

Differential Serum Level of Claudin-3 Identified by iTRAQ is Corroborated by Western Blotting To assess whether claudin-3 is a potential biomarker, independent serum samples were taken of sham (no hemorrhage and no treatment), HS 1 hour (1 hour following hemorrhagic shock), and VPA 1 hour (1 hour following VPA treatment) from individual rats and the level of the candidate biomarker was determined by Western blot with anti-claudin-3 antibody.

Proteins (about 100 µg per lane) were separated by SDS-PAGE on 12% polyacrylamide gels and transferred onto nitrocellulose membranes (Bio-Rad Laboratories, Hercules, Calif.). The membranes were blocked in 0.05% PBS-Tween (PBST) containing 5% milk (Bio-Rad Laboratories, Hercules, Calif.) and then incubated with the primary antibody at 4° C. overnight. The primary antibody was detected by incubation with horseradish peroxidase-coupled secondary antibody (1:3,000 in PBST with 5% milk) at room temperature for 2 hours. Chemiluminescent detection was performed by using Western Lighting Chemiluminescence Reagent Plus (PerkinElmer LAS, Inc., Boston, Mass.). Films were developed using a standard photographic procedure and quantitative analysis of detected bands was carried out by densitometer scanning using VersaDoc Imaging System (BioRad Laboratories, Hercules, Calif.).

In serum from sham and VPA 1 hour groups no claudin-3 was detected. However, there were two bands clearly observed from the HS 1 hour group. One was ~23 kDa and the other one was ~11 kDa (FIG. 4A). The data demonstrated that HS dramatically increases serum levels of claudin-3 and VPA treatment reverses the induction of claudin-3. The results confirm the data from iTRAQ and indicate that claudin-3 is a potential biomarker for HS.

Example 4

Acute Response of Intestinal Claudin-3 Protein to Hemorrhagic Shock and VPA Treatment Claudin-3 is a TJ protein that has important roles in establishing epithelial and endothelial barriers. To find out whether HS and VPA treatment affect claudin-3 protein in TJ of epithelial cells, protein expression was analyzed in intestinal tissue obtained from sham, HS 1 hour (1 hour after hemorrhagic shock), and VPA-treated animals (1 hour, 6 hours, and 24 hours after treatment).

The intestine tissues were collected, homogenized, and protein was extracted using Whole Cell Extraction Kit containing protease inhibitor cocktail. Equal amounts of intestinal lysate were separated on SDS-PAGE and subjected to Western blotting using an antibody against claudin-3 as described herein. Actin was used as an internal control to demonstrate equal protein loading. As shown in FIGS. 5A and 5B, claudin-3 was normally expressed in sham animal intestine. HS markedly decreased the protein level of claudin-3 in the intestine. VPA treatment significantly attenuated the HS-induced reduction of claudin-3 at 1, 6, and 24 hours. The results indicate that HS causes rapid loss of intestinal claudin-3, and VPA treatment protects against loss of claudin-3 from the intestine.

Animals treated with VPA showed normalization of the serum and intestinal claudin-3 profiles, and they survived. In contrast, the untreated animals continued to display an abnormal profile and none of these animals survived the blood loss. Thus, changes in the circulating claudin-3 levels can be used to monitor the response to treatment and to predict the outcome (prognosis).

To assess whether gene expression of claudin-3 responds to HS and VPA treatment, the mRNA expression of rat intestines among the groups of sham, HS and VPA treatment was compared at 1, 6 and 24 hours using RT-PCR methods. As shown in FIGS. 6A and 6B, HS and VPA treatment did not significantly change claudin-3 mRNA expression. These results indicate that HS causes rapid loss of intestinal claudin-3 at protein level, and VPA treatment protects against loss of claudin-3 protein from the intestine.

Example 5

Identification of Novel Serum Biomarkers for the Diagnosis and Treatment of Hemorrhagic Shock Circulating levels of acute-phase proteins may serve as biomarkers to facilitate early diagnosis of HS, determine its severity, and monitor the response to treatment. Treatment with VPA up-regulates various survival pathways and improves outcome. This proteomics study demonstrates that these changes would result in altered levels of serum biomarkers.

Male Wistar-Kyoto rats underwent HS (60% blood loss) followed by treatment with or without VPA (300 mg/kg). Serum samples were obtained at baseline (BL), end of hemorrhage (EH), and after VPA treatment (VPA), and subjected to iTRAQ and analyzed by liquid chromatography-tandem mass spectrometry (LC-MS/MS). A lower confidence bound (LCB) of 1.2-fold change was used for statistical analysis. Tissues were harvested at the end of the experiment. Western blotting was used to validate iTRAQ-identified biomarkers from independent serum and tissue samples.

Identification and quantification of iTRAQ-labeled peptides that mapped to 130 proteins (SwissProt) revealed 12 biomarkers whose serum levels were altered in early HS, and corrected by VPA treatment (Table 2). These biomarkers include KC/GRO, APOA2, AGT, TG, ADAM17, PRSS1, C4A, ZP1, NRP2, SLC13A2, GLP2R, and LHFPL4. Hemorrhage resulted in an increase in KC/GRO, APOA2, ADAM17, PRSS1, C4A, ZP1, NRP2, SLC13A2, GLP2R, and LHFPL4 levels and a decrease in AGT and TG levels. VPA treatment attenuated these alterations, and significantly improved survival.

HS causes early and rapid alterations in the serum levels of KC/GRO, APOA2, AGT, TG, ADAM17, PRSS1, C4A, ZP1, NRP2, SLC13A2, GLP2R, and LHFPL4, in addition to claudin-3. VPA treatment corrects these alterations, and leads to improved survival. These biomarkers can be used to diagnose shock and reflect the effectiveness of a treatment.

TABLE 2

Relative serum levels of protein biomarkers identified by iTRAQ or ELISA

| Biomarker | Baseline (100%) | HS (% of Baseline) | VPA treatment (% of Baseline) | Remark |
|---|---|---|---|---|
| keratinocyte chemoattractant (KC)/human growth-regulated oncogene (GRO) (KC/GRO)* | | | | Also confirmed by ELISA (See FIG. 7) |
| disintegrin and metalloproteinase domain-containing protein 17 (ADAM17) | 1 | 1.28 | 0.93 | |
| apolipoprotein A2 (APOA2) | 1 | 1.39 | 0.61 | |
| anionic trypsin-1 (PRSS1) | 1 | 1.59 | 0.53 | |
| complement C4 (C4A) | 1 | 1.15 | 0.93 | |
| angiotensinogen r (AGT) | 1 | 0.81 | 1.07 | |
| zona pellucida sperm-binding protein 1 (ZP1) | 1 | 1.63 | 0.44 | |
| thyroglobulin (TG) | 1 | 0.78 | 1.5 | |
| neuropilin-2 (NRP2) | 1 | 1.47 | 0.90 | |
| solute carrier family 13 member 2 (SLC13A2) | 1 | 1.50 | 1.05 | |
| glucagon-like peptide 2 receptor (GLP2R) | 1 | 1.28 | 0.88 | |
| lipoma HMGIC fusion partner-like protein 4 (LHFPL4) | 1 | 1.27 | 0.87 | |

*Serum KC/GRO protein was identified by protein array and confirmed by ELISA.

Example 6

Lung Injury Following Hemorrhagic Shock can be Detected Early by Measuring Circulating Biomarker Acute lung injury (ALI) is a serious complication of hemorrhagic shock, which is rarely identified prior to clinical deterioration of the patient. Detection of circulating biomarkers may facilitate early diagnosis and treatment. In this example, an elevated serum level of cytokine-induced neutrophil chemoattractant (CINC), a rat homolog of the human KC/GRO protein, is shown to be an early biomarker for ALI following hemorrhagic shock.

Anesthetized Wistar-Kyoto rats (250-300 g) underwent 40% blood volume hemorrhage over 10 minutes followed by 30 minutes of un-resuscitated shock and were treated with 1) VPA 300 mg/kg or 2) vehicle control. Blood samples were obtained at baseline, following shock, and prior to sacrifice (1 hour, 4 hours, and 20 hours; n=3-4/time point/group). Serum samples were screened for possible biomarkers using a multiplex electrochemiluminescence detection assay, and results were confirmed using ELISA. Additionally, lung tissue lysate was examined for chemokine and myeloperoxidase (MPO) levels as markers for neutrophil infiltration and ALI. Additionally, lung CINC-1 (a chemokine belonging to the IL-8 family that promotes neutrophil chemotaxis) mRNA levels were measured by real-time PCR.

Hemorrhagic Shock

Animals were hemorrhaged 40% of their total blood volume to induce sub-lethal HS, and were sacrificed at 1, 4, and 20 hours following hemorrhage and treatment. This degree of blood loss was selected to allow 100% of animals in all groups to survive until the designated time of sacrifice. Selected laboratory values were measured, and were indicative of moderate HS (mean lactate 0.6 mmol/L at baseline, 4.3 mmol/L after hemorrhage; mean baseline hemoglobin 12.0 g/dL at baseline, 9.6 g/dL after hemorrhage).

Circulating CINC-1

Figure 7:
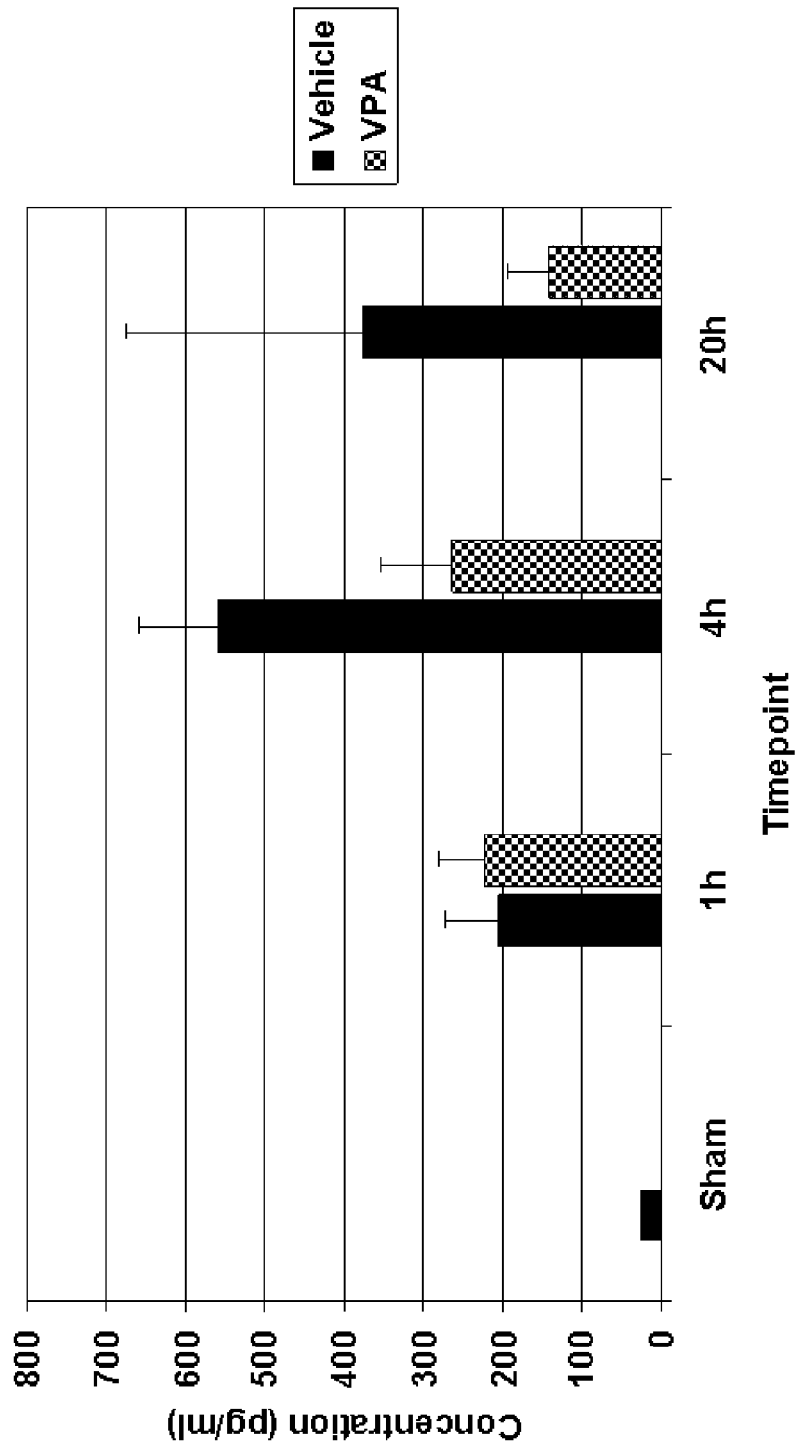
FIG. 7 is a bar graph showing the levels of CINC in serum as assayed using a multiplex electrochemiluminescence assay. Rats were hemorrhaged 40% of their blood volume and treated with VPA 300 mg/kg IV or normal saline vehicle (VEH). Serum was collected at the time of sacrifice (1 hour, 4 hours, and 20 hours) as well from sham animals, and analyzed. Data shown as mean CINC-1 concentration±SEM.

Serum samples (n=3-4/time point/group) were screened using a multiplex electrochemiluminescence assay to determine if there were any changes in circulating cytokines and chemokines Of the seven cytokines analyzed (IL-1β, CINC-1, IL-4, IL-5, TNFα, IFNγ, IL-13), CINC-1 exhibited a robust rise following HS, which appeared to be attenuated by VPA treatment (FIG. 7). Two samples had to be eliminated from the sham group (CINC-1 below the lower limit of detection) and one sample had to be eliminated from the vehicle 20 hour group (CINC-1 coefficient of variation greater than 20%).

Figure 8:
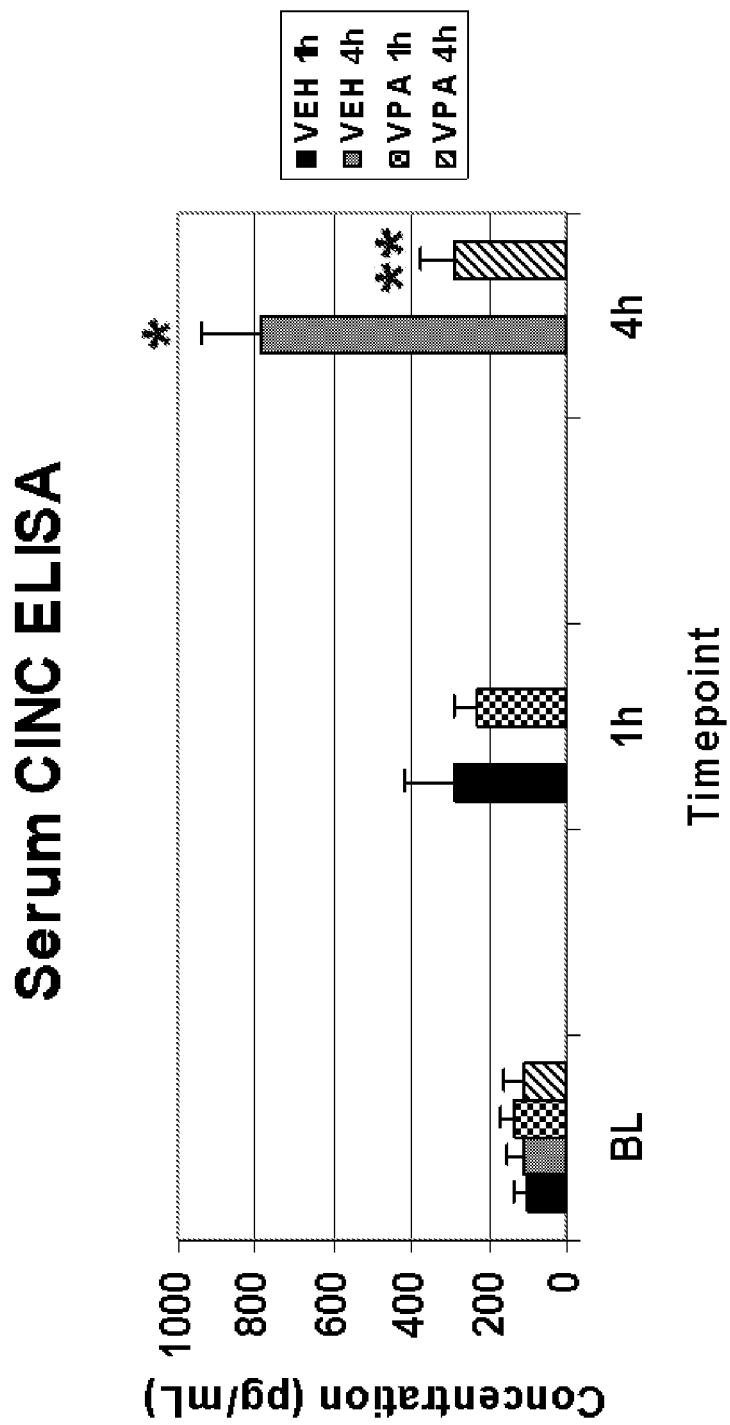
FIG. 8 is a bar graph showing the levels of CINC in serum as assayed by ELISA. Rats were hemorrhaged 40% of their blood volume and treated with VPA 300 mg/kg IV or normal saline vehicle (VEH). Serum was collected for analysis at baseline (BL) and at the time of sacrifice (1 hour and 4 hours). Data shown as mean CINC-1 concentration±SEM. Hemorrhage resulted in a significant increase in serum CINC-1 levels at 4 hours (*p<0.05 vs. BL), whereas VPA treatment significantly attenuated this effect (**p<0.05 vs. VEH 4 hours).

Conventional ELISA was used to confirm the data obtained using the multiplex electrochemiluminescence assay. At baseline, all groups exhibited similar low levels of circulating CINC-1. HS increased the amount of circulating CINC-1, and VPA treatment significantly attenuated this effect at 4 hours (FIG. 8). The other cytokines were either below the lower limit of detection or did not exhibit obvious differences between groups so no further analysis of these cytokines was undertaken.

Lung CINC-1

Figure 9:
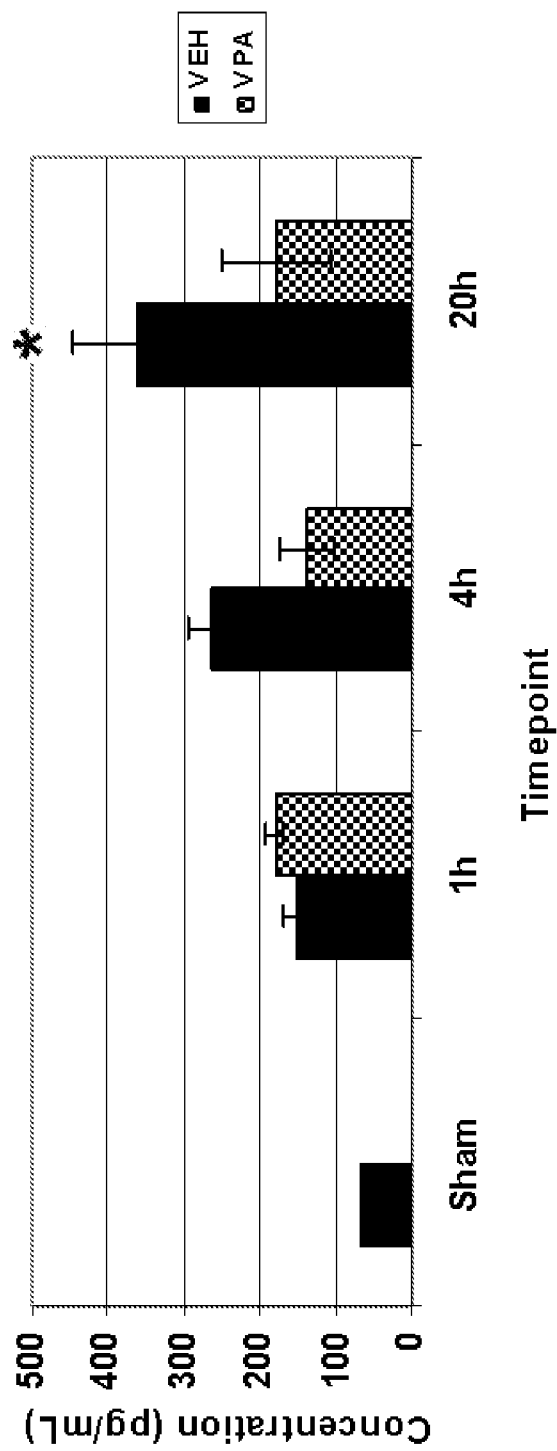
FIG. 9 is a bar graph showing the levels of CINC in lung tissue. Rats were hemorrhaged 40% of their blood volume and treated with VPA 300 mg/kg IV or normal saline vehicle (VEH). Lung tissue was collected for analysis at the time of sacrifice (1 hour, 4 hours, and 20 hours) as well as from sham animals. Data shown as mean CINC-1 concentration±SEM. Hemorrhage resulted in a significant increase in lung CINC-1 levels at 20 hours (*p<0.05 vs. sham). The effects of VPA on lung CINC-1 levels were not statistically significant (p=0.17; comparing VEH vs. VPA at the 20 hour time point).

ELISA was used to measure CINC-1 levels in lung whole tissue extract (n=3-4/time point/group). Sham animals exhibited a low level of CINC-1 in the lung. HS resulted in a gradual increase of CINC-1 in lung tissue, which became significantly different from sham by 20 hours (FIG. 9).

Lung Myeloperoxidase

Figure 10:
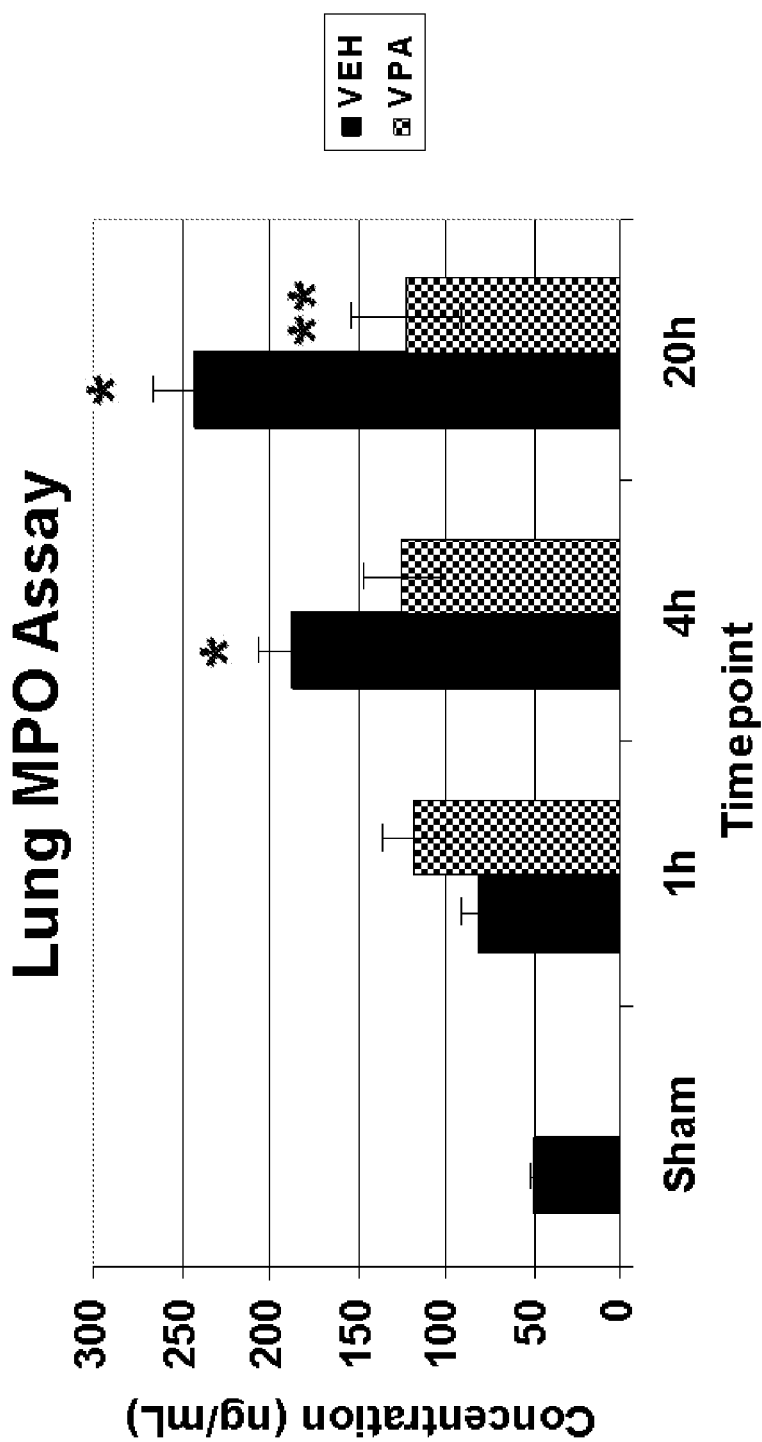
FIG. 10 is a bar graph showing the levels of MPO in lung tissue. Rats were hemorrhaged 40% of their blood volume and treated with VPA 300 mg/kg IV or normal saline vehicle (VEH). Lung tissue was collected for analysis at the time of sacrifice (1 hour, 4 hours, and 20 hours) as well as from sham animals. Data shown as mean MPO concentration±SEM. Hemorrhage resulted in a significant increase in lung MPO levels at 4 hours and 20 hours (*p<0.05 vs. sham), whereas VPA attenuated this effect (**p<0.05 vs. VEH 20 hours).

Myeloperoxidase (MPO) levels were measured in lung whole tissue extract as a marker for neutrophil infiltration (n=3-4/time point/group). Sham animals exhibited low levels of MPO in the lung. HS resulted in a gradual increase of lung MPO levels, which were highest at 20 hours (nearly 5-fold that of sham), and significantly different from sham at 4 hours and 20 hours. VPA treatment significantly attenuated this effect at the 20 hour time point (FIG. 10).

CINC-1 mRNA Levels

Figure 11:
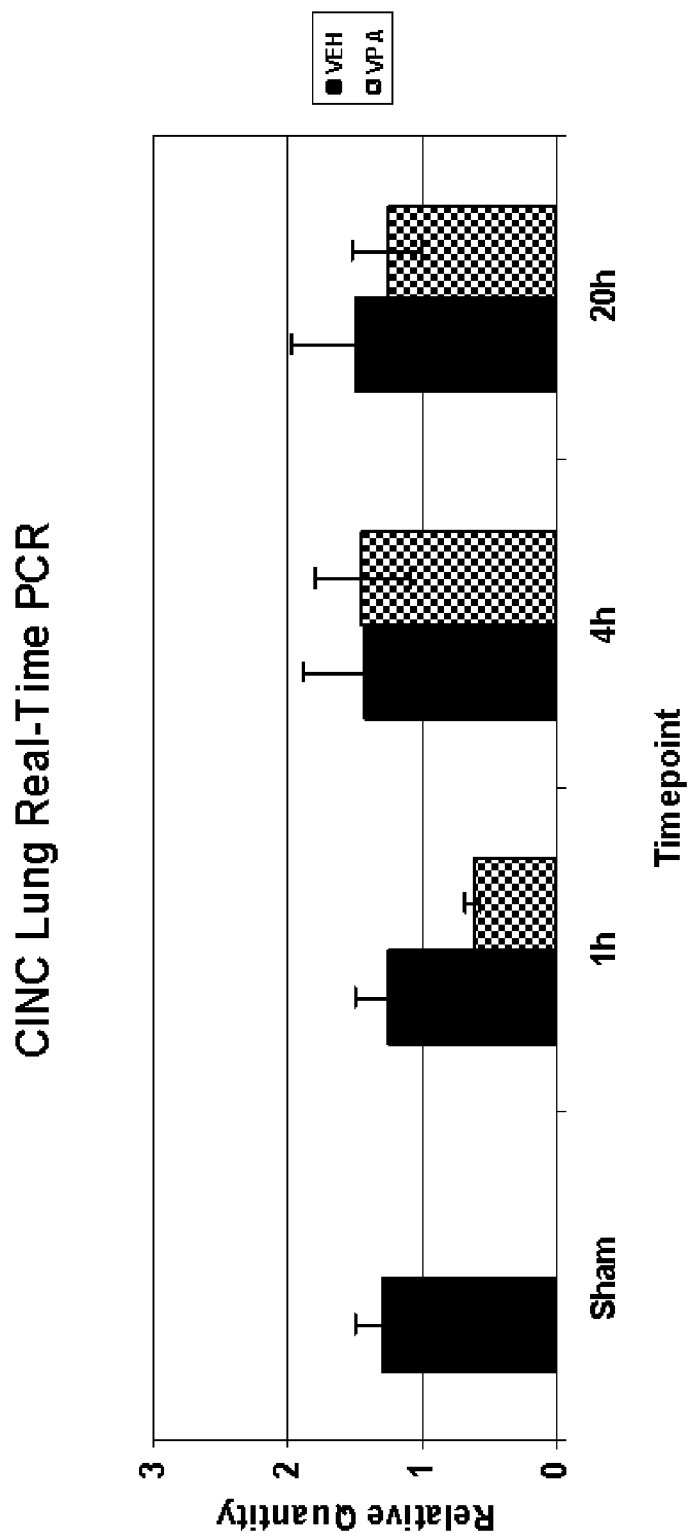
FIG. 11 is a bar graph showing the levels of CINC mRNA in lung tissue. Rats were hemorrhaged 40% of their blood volume and treated with VPA 300 mg/kg IV or normal saline vehicle (VEH). Lung tissue was collected for analysis at the time of sacrifice (1 hour, 4 hours, and 20 hours) as well as from sham animals. Data shown as CINC-1 relative quantity±SEM. There were no significant differences between groups.

To rule out possibility that an increase of CINC-1 protein in lung results from induction of the gene expression, lung tissue was assessed for CINC-1 mRNA levels (n=3-4/time point/group). Hemorrhage had no effect on CINC-1 mRNA levels over time. There were no significant changes between groups (FIG. 11).

RESULTS AND CONCLUSIONS

Serum screening revealed that hemorrhage rapidly altered levels of circulating CINC-1. ELISA confirmed that CINC-1 protein was significantly elevated in the serum as early as 4 hours, and in the lung at 20 hours, following hemorrhage without any significant changes in the CINC-1 mRNA expression. Lung MPO levels were also elevated 4 hours and 20 hours after hemorrhage. VPA treatment attenuated these changes.

Hemorrhage resulted in development of ALI, which was inhibited and reduced with VPA treatment. Circulating CINC-1 levels rose rapidly after hemorrhage, and serum CINC-1 levels correlated with lung CINC-1 and MPO levels. This suggests that circulating CINC-1 could be used as an early marker for the subsequent development of organ inflammation and injury.

HS results in early elevation of serum CINC-1 levels as well as elevation of lung CINC-1 and MPO levels, indicating neutrophil infiltration and inflammation—hallmarks of ALI. Pharmacologic resuscitation with VPA attenuates these effects. CINC-1 is an early marker for HS-induced organ injury, and pharmacologic resuscitation with HDACI such as VPA may offer anti-inflammatory benefits following HS.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of predicting and improving prognosis of a subject suffering from hemorrhagic shock (HS), the method comprising:
   obtaining a sample comprising serum from the subject;
   determining expression levels of keratinocyte chemoattractant (KC)/human growth-regulated oncogene (GRO) (KC/GRO), zona pellucida sperm-binding protein 1 (ZP1), and apolipoprotein A2 (APOA2) in the sample to obtain test values;
   comparing the test values to respective reference values that represent threshold levels of KC/GRO, ZP1, and APOA2;
   identifying the subject as having an increased risk of mortality due to HS if the test values are above the reference values, or identifying the subject as having an increased chance of survival if the test values are below the reference values, and
   administering an effective amount of a vasopressor to the subject identified as having an increased risk of mortality due to HS, thereby improving prognosis of the subject.

2. The method of claim 1, wherein the sample comprises plasma or whole blood.

3. The method of claim 1, wherein the method further comprises:
   determining an expression level of claudin-3 in the sample to obtain a test value;
   comparing the test value to a reference value that represents a threshold level of claudin-3; and
   identifying the subject as having an increased risk of mortality due to HS if the test value is above the reference value, or identifying the subject as having an increased chance of survival if the test value is below the reference value.

4. The method of claim 1, wherein the subject is a human.

5. The method of claim 1, wherein the method further comprises:
   determining an expression level of angiotensinogen r (AGT), thyroglobulin (TG), disintegrin and metalloproteinase domain-containing protein 17 (ADAM17), anionic trypsin-1 (PRSS1), complement C4 (C4A), neuropilin-2 (NRP2), solute carrier family 13 member 2 (SLC13A2), glucagon-like peptide 2 receptor (GLP2R), or lipoma high mobility group protein isoform I-C (HMGIC) fusion partner-like protein 4 (LHFPL4) in the sample to obtain a test value;
   comparing the test value to a respective reference value that represents a threshold level of AGT, TG, ADAM17, PRSS1, C4A, NRP2, SLC13A2, GLP2R, or LHFPL4; and
   identifying the subject as having an increased risk of mortality due to HS if the test value of ADAM17, PRSS1, C4A, NRP2, SLC13A2, GLP2R, or LHFPL4 is above its respective reference value or the test value of AGT or TG is below its respective reference value; or identifying the subject as having an increased chance of survival if the test value of ADAM17, PRSS1, C4A, ZP1, NRP2, SLC13A2, GLP2R, or LHFPL4 is below its respective reference value or the test value of AGT or TG in the subject is above its respective reference value.

6. The method of claim 5, wherein the method comprises determining expression levels of KC/GRO, APOA2, AGT, TG, ADAM17, PRSS1, C4A, ZP1, NRP2, SLC13A2, GLP2R, and LHFPL4; and comparing the test values to respective reference values.

7. The method of claim 1, wherein the levels of KC/GRO and APOA2 are determined by quantitative immunoassay.

8. The method of claim 7, wherein the quantitative immunoassay is selected from the group consisting of enzyme linked immunosorbent assay (ELISA), immunoprecipitation, immunofluorescence, enzyme immunoassay (EIA), radioimmunoassay (RIA), and Western blot analysis.

9. A method of predicting and improving prognosis of a subject suffering from HS, the method comprising:
   obtaining a sample comprising serum from the subject;
   determining expression levels of KC/GRO, ZP1, and APOA2 in the sample to obtain test values;
   comparing the test values to respective reference values that represent threshold levels of KC/GRO, ZP1, and APOA2;
   identifying the subject as having an increased risk of mortality due to HS if the test values are above the reference values, or identifying the subject as having an increased chance of survival if the test values are below the reference values; and
   administering an effective amount of a histone deacetylase 1 (HDAC1) inhibitor to the subject identified as having an increased risk of mortality due to HS, thereby improving prognosis of the subject.

10. The method of claim 9, wherein the sample comprises plasma or whole blood.

11. The method of claim 9, wherein the method further comprises:
    determining an expression level of AGT, TG, ADAM17, PRSS1, C4A, NRP2, SLC13A2, GLP2R, or LHFPL4 in the sample to obtain a test value;
    comparing the test value to a respective reference value that represents a threshold level of AGT, TG, ADAM17, PRSS1, C4A, NRP2, SLC13A2, GLP2R, or LHFPL4; and
    identifying the subject as having an increased risk of mortality due to HS if the test value of ADAM17, PRSS1, C4A, NRP2, SLC13A2, GLP2R, or LHFPL4 is above its respective reference value or the test value of AGT or TG is below its respective reference value; or identifying the subject as having an increased chance of survival if the test value of ADAM17, PRSS1, C4A, ZP1, NRP2, SLC13A2, GLP2R, or LHFPL4 is below its respective reference value or the test value of AGT or TG in the subject is above its respective reference value.

12. The method of claim 11, wherein the method comprises determining expression levels of KC/GRO, APOA2, AGT, TG, ADAM17, PRSS1, C4A, ZP1, NRP2, SLC13A2, GLP2R, and LHFPL4; and comparing the test values to respective reference values.

13. The method of claim 9, wherein the method further comprises:
    determining an expression level of claudin-3 in the sample to obtain a test value;
    comparing the test value to a reference value that represents a threshold level of claudin-3; and
    identifying the subject as having an increased risk of mortality due to HS if the test value is above the reference value, or identifying the subject as having an increased chance of survival if the test value is below the reference value.

14. The method of claim 9, wherein the subject is a human.

15. The method of claim 9, wherein the HDAC1 inhibitor comprises valproic acid (VPA).

16. The method of claim 9, wherein the levels of KC/GRO and APOA2 are determined by quantitative immunoassay.

17. The method of claim 16, wherein the quantitative immunoassay is selected from the group consisting of ELISA, immunoprecipitation, immunofluorescence, EIA, RIA, and Western blot analysis.

18. A method of predicting and improving prognosis of a subject suffering from HS, the method comprising:
    obtaining a sample comprising serum from the subject;
    determining expression levels of KC/GRO, ZP1, and APOA2 in the sample to obtain test values;
    comparing the test values to respective reference values that represent threshold levels of KC/GRO, ZP1, and APOA2;
    identifying the subject as having an increased risk of mortality due to HS if the test values are above the reference values, or identifying the subject as having an increased chance of survival if the test values are below the reference values; and
    administering a treatment for HS to the subject identified as having an increased risk of mortality due to HS, wherein the treatment comprises fluid resuscitation or transfusion of blood or a blood product, thereby improving prognosis of the subject.

19. The method of claim 18, wherein the sample comprises plasma or whole blood.

20. The method of claim 18, wherein the method further comprises:
    determining an expression level of AGT, TG, ADAM17, PRSS1, C4A, NRP2, SLC13A2, GLP2R, or LHFPL4 in the sample to obtain a test value;
    comparing the test value to a respective reference value that represents a threshold level of AGT, TG, ADAM17, PRSS1, C4A, NRP2, SLC13A2, GLP2R, or LHFPL4; and
    identifying the subject as having an increased risk of mortality due to HS if the test value of ADAM17, PRSS1, C4A, NRP2, SLC13A2, GLP2R, or LHFPL4 is above its respective reference value or the test value of AGT or TG is below its respective reference value; or identifying the subject as having an increased chance of survival if the test value of ADAM17, PRSS1, C4A, ZP1, NRP2, SLC13A2, GLP2R, or LHFPL4 is below its respective reference value or the test value of AGT or TG in the subject is above its respective reference value.

21. The method of claim 20, wherein the method comprises determining expression levels of KC/GRO, APOA2, AGT, TG, ADAM17, PRSS1, C4A, ZP1, NRP2, SLC13A2, GLP2R, and LHFPL4; and comparing the test values to respective reference values.

22. The method of claim 18, wherein the method further comprises:
    determining an expression level of claudin-3 in the sample to obtain a test value;
    comparing the test value to a reference value that represents a threshold level of claudin-3; and
    identifying the subject as having an increased risk of mortality due to HS if the test value is above the reference value, or identifying the subject as having an increased chance of survival if the test value is below the reference value.

23. The method of claim 18, wherein the subject is a human.

24. The method of claim 18, wherein the levels of KC/GRO and APOA2 are determined by quantitative immunoassay.

25. The method of claim 24, wherein the quantitative immunoassay is selected from the group consisting of ELISA, immunoprecipitation, immunofluorescence, EIA, RIA, and Western blot analysis.

* * * * *

SEQUENCE LISTING

```
<160> NUMBER OF SEQ ID NOS: 1

<210> SEQ ID NO 1
<211> LENGTH: 9
<212> TYPE: PRT
<213> ORGANISM: Artificial Sequence
<220> FEATURE:
<223> OTHER INFORMATION: laboratory-synthesized peptide

<400> SEQUENCE: 1

Ala Lys Ile Thr Ile Val Ala Gly Val
1               5
```